United States Patent [19]

Hostetler et al.

[11] Patent Number: 5,411,947
[45] Date of Patent: May 2, 1995

[54] METHOD OF CONVERTING A DRUG TO AN ORALLY AVAILABLE FORM BY COVALENTLY BONDING A LIPID TO THE DRUG

[75] Inventors: Karl Y. Hostetler, Del Mar; Raj Kumar, San Diego, both of Calif.

[73] Assignee: Vestar, Inc., San Dimas, Calif.

[21] Appl. No.: 991,166

[22] Filed: Dec. 16, 1992

Related U.S. Application Data

[63] Continuation-in-part of Ser. No. 373,088, Jun. 28, 1989, Pat. No. 5,223,263, Ser. No. 440,898, Nov. 22, 1989, Pat. No. 5,194,654, and Ser. No. 932,231, Aug. 19, 1992, abandoned.

[51] Int. Cl.$^6$ .............. A01N 43/04; A01N 37/18; A61K 37/00; A61K 31/43
[52] U.S. Cl. ..................... 514/43; 514/50; 514/885; 514/12; 514/2; 514/18; 514/192; 514/199; 514/200
[58] Field of Search ............... 536/26.5; 514/43, 885, 514/12, 2, 18, 192, 199, 200, 50

[56] References Cited

U.S. PATENT DOCUMENTS

| | | | |
|---|---|---|---|
| 4,046,914 | 9/1977 | Hallgren et al. | 424/312 |
| 4,471,113 | 9/1984 | MacCoss | 536/29 |
| 4,634,719 | 1/1987 | Takaishi et al. | 51/772 |
| 5,071,839 | 12/1991 | Liu | 514/25 |
| 5,194,654 | 3/1993 | Hostetler et al. | 558/152 |

FOREIGN PATENT DOCUMENTS

| | | |
|---|---|---|
| 457570A1 | 11/1991 | European Pat. Off. |
| 9119726 | 12/1991 | WIPO |
| 9219233 | 11/1992 | WIPO |

OTHER PUBLICATIONS

Hostetler, et al., "Synthesis and Antiretroviral Activity of Phospholipid Analogs of Azidothymidine and other Antiviral Nucleosides", *The Journal of Biological Chemistry*, 265:11:6112–6117, Apr. 1990.

Hostetler, et al., "Phosphatidylazidothyimidine", *The Journal of Biological Chemistry*, 266:18:11714–11717, Jun. 1990.

Hong, et al., 79th Annual Meeting of the American Assoc. for Cancer Research, vol. 29, p. 359, 1988.

Hostetler, et al., "Greatly Enhanced Inhibition of Human Immunodeficiency . . .", *Antimicrob. Agents Chemother.*, 36:9:2025, 1992.

Ryu, et al., "Phospholipid–Nucleoside Conjugates. 3.$^1$ Synthesis and Preliminary . . .", *J. Med. Chem.* 25:1322–1329, 1982.

Dietrich, et al., "Enhancement of Host Resistance against Virus Infections . . .", *Int. J. Immunopharmacol.*, 8:8:931–942, 1986.

Hong, et al., "1-β-D-Arabinofuranosylcytosine Conjugates of Ether . . . ", *Lipids*, 26:12:1437–1444, 1991.

Dixon, R., et al. (1991) "AICA-Riboside: safety, tolerance, and pharmacokinetics of a novel adenosine-regulating agent", *J. Clin. Pharmacol.*; 31:342–347.

Larder, B. A. et al. (1989) HIV with reduced sensitivity to zidovudine (AZT) isolated during prolonged therapy, *Science* 243; 1731–1734.

Ruprecht, R. M., et al., (1986) "Suppression of mouse viraemia and retroviral disease by 3'-azido-3'-deoxythymidine" *Nature* 323:467–469.

*Primary Examiner*—David M. Naff
*Assistant Examiner*—Mike Miller
*Attorney, Agent, or Firm*—Knobbe, Martens, Olson & Bear

[57] ABSTRACT

The oral delivery of many classes of drugs is facilitated by converting drugs having suitable functional groups to 1-O-alkyl-, 1-O-acyl-, 1-S-acyl, and 1-S-alkyl-sn-glycero-3-phosphate derivatives. The method confers the ability to be absorbed through the digestive tract to drugs that are not orally bioavailable in the non-derivatized state, and enhances the effectiveness of drugs that are poorly absorbed or rapidly eliminated. The method provides orally bioavailable lipid prodrugs of pharmaceutical compounds having diverse physiological activities, including anticancer and antiviral agents, anti-inflammatory agents, antihypertensives and antibiotics. Potency of the lipid prodrugs is comparable to that of the corresponding non-derivatized drugs.

12 Claims, 25 Drawing Sheets

METHOD OF CONVERTING A DRUG TO AN ORALLY AVAILABLE FORM BY COVALENTLY BONDING A LIPID TO THE DRUG

This application is a continuation-in-part of the following U.S. applications: Ser. No. 07/373,088, filed Jun. 28, 1989, and titled "Lipid Derivatives of Antiviral Nucleosides", now U.S. Pat. No. 5,223,263; Ser. No. 07/440,898, filed Nov. 22, 1989, and titled "Lipid Derivatives of Phosphonoacids for Liposome Incorporation and Method of Use", now U.S. Pat. No. 5,194,654; and Ser. No. 07/932,231, filed Aug. 19, 1992 now abandoned, and titled "Lipid Prodrugs of Salicylate and other Non-Steroidal Anti-Inflammatory Drugs." These applications are hereby incorporated by reference in their entirety.

This application relates to methods of drug delivery. It relates particularly to methods for facilitating the oral bioavailability of drugs.

BACKGROUND OF THE INVENTION

The oral route is the most ancient method of drug administration; it is also the safest, most convenient, and most economical. Drugs administered orally can be absorbed through the oral mucosa or through the lining of the stomach and intestines; however, the rate of absorption depends on the ability of the drug to pass through the lipoid barrier of epithelial membranes. For example, alcohol, a lipid soluble, non-ionic compound, is rapidly absorbed into the bloodstream by diffusion across the gastric mucosa. Weak acids are also well absorbed through the lining of the stomach, while weak bases are absorbed mainly in the intestine. Drugs that are ionized, or lipid insoluble, for example, quaternary ammonium compounds and streptomycin, are poorly absorbed in the digestive tract, and must be administered by injection. There are several disadvantages to the injection of drugs. Strict asepsis must be maintained in order to avoid infection, an unintentional intravascular injection may occur, injection may be painful, and it is difficult for the patient. Parenteral administration is also more expensive.

Under normal circumstances, intact dietary lipids, mostly triglycerides and diglyceride phospholipids, are not readily absorbed through the intestinal mucosa. Phospholipids are present physiologically in the gut as phosphatidylcholine, phosphatidylethanolamine, phosphatidylinositol, phosphatidylserine, phosphatidylglycerol, and phosphatidic acid. The normal physiological mechanism for lipid absorption requires conversion of the phosphatidyl forms of phospholipid to lysophospholipids, by removal of the sn-2 acyl group by the hydrolytic action of the pancreatic enzyme phospholipase $A_2$ on the sn-2 acyl ester bond. Conversion of lipids to phospholipids and then to lysophospholipids thus provides the normal mechanism for absorption and transport of lipids from the gut, and accounts for the uptake of several grams of phospholipid per day.

It would be therapeutically useful to convert drugs that are not absorbed through the intestine because of their chemical structure to orally bioavailable prodrug forms, thus eliminating the inconvenience and expense of parenteral administration of these drugs.

SUMMARY OF THE INVENTION

According to the invention there is provided a method of converting a drug, or other pharmaceutical compound, that is unavailable or poorly available through the oral route to an orally available form, comprising preparing a lipid derivative of the pharmaceutical compound, the lipid derivative comprising a 1-O-alkyl-sn-glycerol-3-phosphate group, a 1-O-acyl-sn-glycerol-3-phosphate group, a 1-S-alkyl-sn-glycerol-3-phosphate group, or a 1-S-acyl-sn-glycerol-3-phosphate group covalently linked to a functional group of the drug either directly through a phosphate ester or through a linker molecule; whereby the oral bioavailability and/or tissue levels of the administered pharmaceutical compound are enhanced. A preferred lipid prodrug, comprising a 1-O-alkyl-sn-glycerol-3-phosphate derivative of a drug, has the structure of formula [I]. In particularly preferred embodiments of the method of the invention, the pharmaceutical compound is an anticancer nucleoside having a carboxyl, hydroxyl, or amino group available for covalent binding; for example, 9-β-D-arabinofuranosylcytosine (ara-C), 5-fluorouridine, 6-mercaptopurine riboside, 9-β-D-arabinofuranosyladenine (ara-A), 2'-arafluoro-2-chlorodeoxyadenosine or 5-amino-4-imidazole carboxamide ribonucleoside (AICA-riboside). In alternative preferred embodiments, the pharmaceutical compound is a therapeutic peptide, or a peptidomimetic of from 3 to 35 amino acid residues or analogues thereof. In particular embodiments of this aspect of the invention, the pharmaceutical compound is n-muramyl tripeptide or enalkiren. In yet other embodiments, D is selected from the group consisting of antibiotics of the penicillin and cephalosporin class; for example, D is selected from the group consisting of penicillin G, cefazolin, ceftazidime, ceftriaxone, and piperacillin.

According to another aspect of the invention there is provided a method of enhancing the pharmacokinetic properties of an orally administered pharmaceutical compound, comprising preparing a lipid derivative of the pharmaceutical compound, the lipid derivative comprising a 1-O-alkyl-sn-glycerol-3-phosphate, a 1-O-acyl-sn-glycerol-3-phosphate, a 1-S-alkyl-sn-glycerol-3-phosphate, or a 1-S-acyl-sn-glycerol-3-phosphate group covalently linked to a functional group of the compound either directly through a phosphate ester or through a linker molecule, whereby the metabolic clearance of the compound is decreased, and the physiological half-life of the compound is extended. In embodiments of this aspect of the invention, the pharmaceutical compound is 3'-azido-3'-deoxythymidine (AZT) or 3'-azido-3'-acycloguanosine (ACG).

According to yet another aspect of the invention there are provided antineoplastic prodrugs, comprising taxol or a substituted taxol compound, covalently bound to a phospholipid compound. In preferred embodiments, the taxol prodrug comprises a phospholipid compound selected from the group consisting of phosphatidylglycerols, 1-O-alkyl-sn-glycero-3-phosphatidic acids, 1-O-acyl-sn-glycero-3-phosphatidic acids, 1-S-alkyl-sn-glycero-3-phosphatidic acids, and 1-S-acyl-sn-glycero-3-phosphatidic acids. In preferred embodiments of this aspect of the invention, the taxol compound is a taxol analogue having lipophilic substituents at the β-amino group of the taxol side chain. These lipophilic substituents can be selected from the group consisting of benzoyl, pivaloyl, acetate, peptides, or amino acids. The taxol analogue side chain can further comprise an aliphatic $C_{1-10}$ hydrocarbon group to further increase lipophilicity.

According to another aspect of the invention there are provided taxol side chains bound to a phospholipid and having the structure of formula II, disclosed herein.

According to yet another aspect of the invention there are provided methods of synthesizing a lipid derivative of taxol or a substituted taxol compound, comprising the steps of (a) covalently attaching a phospholipid through a phosphate group to the amino alcohol or hydroxy carboxylic acid groups of the taxol side chain, the propanoic acid group of said side chain being protected by esterification, thus forming a lipid derivative of said side chain; (b) removing the protective group from said propionic acid group; and (c) coupling the lipid derivative of the taxol side chain through the propionic acid group to the allylic alcohol group of baccatin III or 10-deacetyl baccatin.

In another embodiment of this aspect of the invention there is provided a method of synthesizing phospholipid derivatives of taxol or taxol-related compounds, comprising the steps of (a) providing a acyl or alkyl substituted-sn-glycero-sn-3-phosphate and a β-amino-α-hydroxy-benzene propanate ester; (b) linking the glycero-3-phosphate and the benzene propanate ester through a covalent bond between the phosphate group of the phosphatidic acid and the α-hydroxyl group of the benzene propanate ester; (c) de-esterifying the benzene propanate ester group of the lipid derivative of (b) by hydrolysis; (d) linking the lipid derivative of (c) to a taxol related group by condensation of the propanoic acid group of the derivative and the 13—OH group of a taxol ring skeleton.

In preferred embodiments of either of the methods disclosed the acyl or alkyl-substituted glycero-3-phosphate is a 1-O-alkyl-sn-glycero-3-phosphate. In particularly preferred embodiments, the 1-O-alkyl-sn-glycero-3-phosphate is 1-O-octadecyl-sn-glycero-3-phosphate.

BRIEF DESCRIPTION OF THE DRAWINGS

FIG. 1 is a graph showing the comparative levels of AZT in plasma.

FIGS. 2, 3, and 4 are graphs showing the comparative levels of AZT in the stomach, duodenum and jejunum respectively.

FIGS. 5, 6, and 7 are graphs showing the comparative levels of AZT in the liver, spleen and lymph nodes respectively.

FIG. 16: representative antineoplastic agents (a) actinomycin D; (b) daunomycin; (c) etoposide; (d) taxol.

FIG. 17: representative anti-infective agents (a) kanamycin A; (b) neomycin B; (c) amphotericin B.

FIG. 18: representative antiviral agents (a) 5-F-3'-thia-2',3'-dideoxycytidine; (b) foscarnet; (c) ganciclovir.

FIG. 19: representative therapeutic peptides (a) desmopressin; (b) goserelin; (c) muramyl dipeptide; and (d) enalkiren.

FIG. 20: representative drugs having other therapeutic applications (a) morphine; (b) cyclosporine.

DETAILED DESCRIPTION OF THE INVENTION

Figure 1:
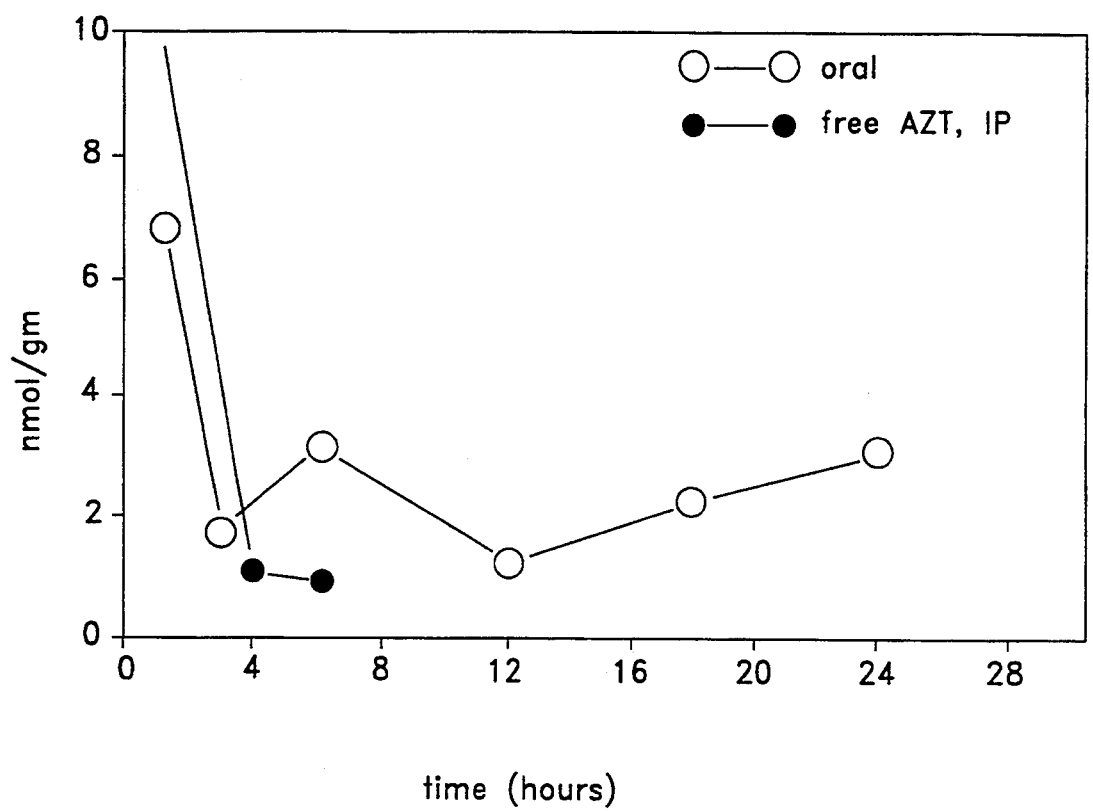
FIGS. 1 through 6 demonstrate the pharmacokinetics of orally administered 1-O-alkyl-sn-glycero-3-phosphate derivatives of drugs by graphical comparisons of the concentration of 3'-azido-3'-deoxythymidine (AZT) in specific tissues of animals treated by oral administration of 1-O-octadecyl-sn-glycero-3-P-AZT[$^3$H] (batyl-P-AZT-[$^3$H]), and those treated by intraperitoneal administration of free AZT.

The invention provides a method for facilitating the transport and absorption by the oral route of several classes of drugs by converting these drugs to lipid prodrugs. A number of drugs that have poor oral bioavailablity can be made suitable for oral administration by conversion to phospholipid derivatives, particularly to monoglyceride phospholipid derivatives, wherein an alkyl group is attached to the 1-position of the glycerol moiety by an ether linkage. The strategy is generally applicable to any drug which has a chemical group capable of covalently binding to a phosphate group or capable of covalently binding to a linking group that can covalently bind to a phosphate group. As disclosed herein, drugs having an available hydroxyl, sulfhydryl, carboxyl or amine group can be covalently linked, by either strategy, to a phosphate group of a 1-O-alkyl-sn-glycero-3-phosphate, or to 1-O-acyl, 1-thioether, and 1-thioester analogs to promote oral absorption of the drug. The linking group is a multifunctional molecule having the required covalent binding properties; for example, an hydroxylated carboxylic acid, or a polypeptide.

The alkyl group of the monoglyceride of the phospholipid derivatives of the invention can be a straight, branched, or cyclic hydrocarbon chain, having from 2 to 24 carbons, and can be saturated or unsaturated with up to six double bonds. Preferably the alkyl group has 8 to 20 carbon atoms. Alkyl groups having from 14 to 18 carbon atoms are most preferred. The alkyl group is attached to the glycerol moiety by an ether or vinyl ether bond.

The preferred lipid derivatives used in the method of the invention are of the formula

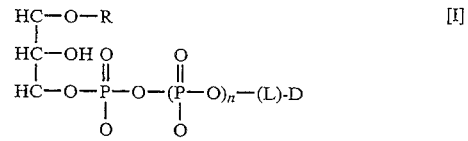

wherein R is a substituted or unsubstituted, saturated or unsaturated, straight or branched chain, or cyclic $C_{1-24}$ alkyl group, covalently linked to the glycerol moiety in an ether linkage;

n = 0 to 2;

L is a linking molecule, of the formula X—(CH$_2$)$_n$—Y wherein X and Y are functional groups independently selected from hydroxyl, sulfhydryl, carboxyl and amine groups, and n = 1 to 24; or L is absent; and D is a therapeutic compound having a functional group selected from the group consisting of hydroxyl, sulfhydryl, carboxyl, or amino groups.

Copending applications Ser. Nos. 07/373,088; 07/730,273; 07/440,898; and 07/734,434 disclose lipid prodrugs having 1-O-alkyl-sn-glycero-3-phosphate moieties.

Linking groups can be any of several molecules having multifunctional groups comprising hydroxyl, sulfhydryl, carboxyl, and amino groups. Particularly suitable for use as linkers are:

(1) the amino alcohols, having the general structure HO—$(CH_2)_n$—$NH_2$, where n=1 to 24, preferably where n=2 or 3, and suitable for insertion at the carboxyl group of a candidate drug which is an active drug moiety or a chemically modified drug. A monoglyceride phosphorylethanolamine is a naturally occurring phospholipid that incorporates a linker of the amino alcohol type, and a 1-O-alkyl-sn-glycerophosphorylethanolamine can be conveniently coupled to drugs having an available carboxyl group to prepare a lipid prodrug of the invention.

(2) the hydroxyalkyl carboxylic acids, having the general structure HO—$(CH_2)_n$—COOH, where n=1 to 12, and suitable for insertion at the amino group of an active candidate drug. Naturally occurring molecules such as hydroxy fatty acids, beta-hydroxybutyric acid, and hydroxyaminoacids such as serine and hydroxyproline may also be conveniently used.

The present invention provides a means for improving the usefulness, efficacy, biological half life, transport across cellular membrane and oral bioavailabities of any drug having a chemical structure suitable for binding as described herein. The method of the invention is advantageously applicable to drugs that are poorly bioavailable, and that must otherwise be administered parenterally. Examples of the variety of therapeutic classes of drugs that can be effectively administered by the oral route comprise 1-O-alkyl, 1-O-acyl-, 1-S-alkyl- (thiether), or 1-S-acyl(thioester) phospholipid derivatives of:

(a) anticancer agents, comprising nucleoside analogues, for example, 9-S-D-arabinofuranosylcytosine (hereinafter, cytosine arabinoside or ara-C), 9-$\beta$-D-arabinofuranosyladenine (hereinafter, adenine arabinoside or ara-A), 5-fluorouridine, 6-mercaptopurine riboside, or 2'-ara-fluoro-2-chlorodeoxyadenosine;

(b) antiviral nucleosides, particularly the 1-O-alkyl phospholipid derivatives of those antiviral nucleosides disclosed in U.S. application Ser. No. 07/373,088, which is hereby incorporated by reference;

(c) therapeutic peptides or peptidomimetics, or peptides that are enzyme inhibitors, comprising D-amino acids, L-amino acids, or amino acid analogues, and having up to about 35 amino acids, preferably less than 6 amino acids, or analogues thereof, particularly the lipid derivatives disclosed in U.S. application Ser. No. 07/734,434, which is hereby incorporated by reference. In a preferred embodiment of this species, a 1-O-alkyl-sn-glycero-3-phosphate derivative of desmopressin, n-muramyl tripeptide, or enalkiren is synthesized and administered orally;

(d) antibiotics, particularly those of the penicillin and cephalosporin class, including penicillin G, cefazolin, ceftazidime, ceftriaxone, or piperacillin.

(e) phosphonoacid compounds, particularly the 1-O-alkyl phospholipid derivatives of phosphonoformic acid and phosphonoacetic acid, and nucleoside phosphonates disclosed in U.S. application Ser. No. 07/440,898;

(e) AICA-riboside (5-amino-4-imidazole carboxamide ribonucleoside), a drug used parenterally for the treatment of ischemic heart disease, and in the treatment of arthritis, autoimmune disease, psoriasis, and other inflammatory conditions, and which is poorly available (<5%) when administered orally in solution (Dixon, R. et al., 1991). Other drugs of this type are 5-amino-(1-beta-D-ribofuranosyl) imidazole carboxamide or 1-beta-D-ribofuranosyl 1,2,4-triazole carboxamide, which are used for the treatment of allergy, including asthma and urticaria eczema; autoimmune disease, including Lesch-Nyhan disease; and cardiac disorders related to restricted blood flow.

(f) non-steroidal anti-inflammatory compounds, particularly the 1-O-alkylphospholipid derivatives of these compounds disclosed in U.S. application Ser. No. 07/932,231. compounds disclosed in U.S. application Ser. No. 07/932,231.

Table 1 lists preferred drug candidates for the method of the invention according to therapeutic class.

TABLE 1

| Candidate Drugs for Preparation of Orally Bioavailable Lipid Prodrugs | |
|---|---|
| THERAPEUTIC CLASS | MERCK INDEX |
| I. Antineoplastic agents | |
| actinomycin D | |
| bleomycin | 1324 |
| cisplatin and Pt analogues: | |
| carboplatin, iproplatin | 2319,1828 |
| cytosine arabinoside | 2790 |
| daunorubicin | 2825 |
| doxofluoridine | 3426 |
| doxorubicin | 3428 |
| etoposide | 3842 |
| floxuridine | 4045 |
| mithramycin | |
| mitomycin C | 6133 |
| mitoxanthrone | 6135 |
| pentostatin (deoxycoformycin) | 7091 |
| phosphonoacids | |
| streptozotocin | 8794 |
| taxol and taxotere | 9049 |
| vinca alkaloids: | |
| vincristine, | 9891 |
| vinblastine | 9887 |
| vindesine | 9892 |
| II. Anti-Infectives | |
| aminoglycosides: | |
| netilmycin, | 6389 |
| amikacin, | 416 |
| gentamycin, | 4284 |
| streptomycin, | 8786 |
| kanamycin A, | 5161 |
| tobramycin. | 9413 |
| neomycin B | 6369 |
| plicamycin | 7510 |
| amphotericin B | 620 |
| vancomycin | 9836 |
| III. Antivirals | |
| 3'-deoxy, 3'-azidothymidine (AZT; anti-HIV) | 139 |
| acyclovir (herpes simplex, anti-HSV) | |
| foscarnet | 4166 |
| ganciclovir (anti-CMV) | 4262 |
| idoxuridine (anti-HSV keratitis) | 4262 |
| ribavarin | 8199 |
| 5-fluoro-3'-thia-2',3'-dideoxycytidine (anti-HBV, HIV) | 9599 |
| trifluridine (herpes group, eye) | |

TABLE 1-continued

Candidate Drugs for Preparation of Orally Bioavailable Lipid Prodrugs

| THERAPEUTIC CLASS | MERCK INDEX |
|---|---|
| vidarabine (HSV encephalitis) | 9881 |
| IV. Short Peptides | |
| corticotropin (ACTH) | 127 |
| calcitonin | 1640 |
| desmopressin (DDAVP) | 2904 |
| gonadotropin RH (LH-RH) | 5354 |
| goserelin (LHRF) | 4433 |
| insulin | 4887 |
| lypressin | 5503 |
| beta-melanotropin ($\beta$-MSH) | 6206 |
| alpha-melanotropin ($\alpha$-MSH) | 6206 |
| muramyl dipeptide | 6214 |
| oxytocin | 6934 |
| vasopressin | 9843 |
| FK-506 | |
| octreotide | 6682 |
| enalkiren (renin inhibitor) | |
| protease inhibitors | |
| V. Miscellaneous Agents | |
| morphine (narcotic analgesic) | 6186 |
| prostaglandins | 7891 |
| leukotrienes | 5339 |
| cyclosporine (immunosuppressive) | 2759 |

A significant aspect of the compounds of the invention and related methods for oral administration of drugs is that 1-O-alkyl-, 1-O-acyl-, 1-S-alkyl-, and 1-S-acylglycerophosphate derivatives require no metabolic conversions for oral absorption. These lipid prodrugs are in this way distinct from phosphatidyl derivatives, for which metabolic processing requires preliminary conversion to a lysophospholipid. Furthermore, the alkyl group at the 1-position of the glycerol moiety of the 1-O-alkyl derivative cannot be degraded by intestinal lysophospholipases because of the ether bond linking the alkyl group to the glycerol structure. This metabolic feature prevents digestive degradation and facilitates the intestinal uptake of the intact 1-O-alkyl-sn-glycero-3-phosphate drug conjugate together with other lysophospholipids that are undergoing membrane transport in the small intestine. The 1-O-acyl and the corresponding thioether and thioester analogs may also be absorbed substantially but are less preferred in applications wherein this property is required.

Coupling of Lipid Moiety to a Candidate Drug

The compounds of the invention are formed according to synthetic procedures which couple a 1-O-alkyl-sn-glycero-3-phosphate, or 1-O-acyl, 1-thioether, or 1-thioester analogs thereof to a drug or which couple a 1-O-alkyl monoglyceride. or 1-O-acyl, 1-thioether, or 1-thioester analogs thereof, to a phosphorylated functional group of a drug.

The 1-O-alkyl glycerol moiety, or any other analog described above, and the drug can be covalently linked through mono-, di-, or triphosphate groups at the sn-3position of the glycerol structure. When the 1-O-alkyl glycerol and the drug are joined through a linking group, the linker molecule is conveniently attached to the terminal phosphate of, for example, 1-O-alkyl-sn-glycero-3-phosphate. In either case the candidate drug has an available functional group.

A reaction is typically carried out at a temperature of 25° to 60° C., preferably 30° to 50° C. for a period of from 2 to 25 h, preferably 8 to 10 h. N,N'-dicyclohexyl-carbodiimide (DCC) is added in measured portions generally over a period of 0.5 to 3 h, preferably 0.75 to 1.5 h.

The reaction mixture is worked up by addition of water and azeotroped by successive additions of toulene and ethanol. The resulting crude product is purified by ion exchange and silica chromatography to afford the desired compound with the desired purity.

The process of the invention is preferably conducted in the liquid phase. Upon addition of either triisopropyl-benzenesulfonyl chloride (TIPS) or N,N'-dicyclohexyl-carbodiimide (DCC), the reaction mixture is heated to a temperature of 30° to 60° C. It is noted that the presence of equivalent, (or more than stoichiometric), amounts of either TIPS or DCC does not impede the course of the reaction.

The temperature of the reaction mixture can rise up to its boiling point.. The heat of the reaction can be removed by external cooling of the reaction vessel or by means of a cooled reflux condenser.

Suitable solvents for the reaction are amines or derivatives thereof. Preferred solvents include tertiary amines such as diisopropylethylamine, triethylamine, tributylamine, or heterocyclic amines such as pyridine or picolines.

1-O-alkyl analogs of the invention, for example 1-O-octadecyl-sn-glycero-3-phosphate derivatives, or any of the other 1-O-acyl or 1-S-acyl or 1-S-alkyl analogs, can be produced by any of the synthetic organic procedures known to those in the art, for example, condensation of batyl alcohol and the monophosphate of the drug candidate such as ara-C monophosphate as described in Example 2 (compound IIa). An alternative approach links the monophosphate of batyl alcohol to a candidate drug in the presence of a condensing agent such as DCC or TPS (Example 5).

In another variation of the method, 1-O-octadecyl-2-benzyl-sn-glycero-3-phosphate was condensed with ara-C while the hydroxy group in 2-position of the batyl alcohol was protected as the benzyl ether. Subsequent Lewis acid catalyzed debenzylation, afforded the orally bioavailable batyl-P-ara-C (Example 5).

Lipid Prodrug Derivatives of Taxol-Related Compounds

Lipid derivatives of taxol are prepared according to a procedure wherein the amino alcohol and hydroxy carboxylic acid units of the taxol side chain are covalently attached to a phosphatidic acid, preferably a 1-O-alkyl glycerophosphate as set forth in Examples 13 through 16. The lipid or 10-deacetyl baccatin III. The side chain can be derivatized by the insertion of an aliphatic group $(CH_2)_n$ to increase lipophilicity.

According to the general procedure, a substituted $\beta$-amino-$\alpha$-hydroxy-benzene propanoate is covalently linked to a phosphatidylglycerol or a 1-O-alkyl- or 1-O-acyl-2-benzyl-sn-glycero-3-phosphatidic acid in the presence of a condensing agent, such as DCC, to provide compounds of the formula:

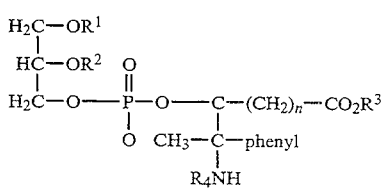

wherein
R[1] and R[2] are the same or different and are straight or branched, saturated or unsaturated $C_8$-$C_{18}$ acyl or alkyl groups; or R[2] can be benzyl or H;
R[3] is any hydrolyzable ester group, for example, methyl, ethyl, or pivaloyl;
R[4] is benzoyl, pivaloyl, acetate, peptides, or amino acids; and
n is 0–10.

In alternative embodiments, $R_1$ and $R_2$ are attached to the glycerol group by thioester or thioether bonds.

In a preferred embodiment, R[1] is an ether-linked batyl group, and R[2] and R[4] are benzyl, and an 1-O-alkyl-2-benzyl-sn-glycero-3-phosphate is condensed with a β-(benzoylamino)-α-hydroxybenzene propanoate ester to form a lipid derivative of the taxol side chain. The propanoate ester is then hydrolyzed to yield the propanoic acid which is ready for coupling with baccatin III, or 10-deacetyl baccatin, having the formula:

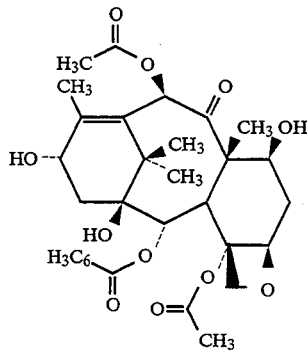

baccatin III

OR

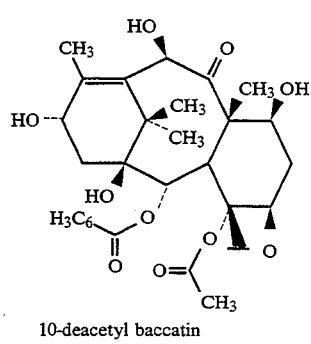

10-deacetyl baccatin to form an orally bioavailable taxol compound.

Lipids comprising fatty acids, fatty alcohols, glycerides, and phospholipids for use in preparing the lipid prodrugs of the invention may be purchased from commercial suppliers (Avanti Polar Lipids, Inc., Pelham, Ala.; or Genzyme Corp., Cambridge, Mass.) or may be synthesized according to known methods. 1-O-octadecyl-sn-glycerol (batyl alcohol) is available from Sigma, St. Louis, and a 2-benzyl derivative of batyl alcohol is available from Bachem, Inc., Basel, Switzerland. Other lysophosphatidic acids useful in preparing the prodrugs of the invention are available from Genzyme, Cambridge, Mass. The drugs to which these lipids are covalently linked can be purchased from the pharmaceutical manufacturers.

It is important that all traces of water be removed from the reactants in order for the coupling reactions to proceed. Therefore, the lipids are first either freeze-dried by solvent evaporation under vacuum, or in a vacuum oven over $P_2O_5$. The reactions are also carried out under an inert gas, such as, for example, argon.

The synthetic reactions are followed using thin layer chromatography (TLC) with appropriate solvents. When the reaction is complete as determined by TLC, the product is extracted with an organic solvent and purified by chromatography on a support suitable for lipid separation, for example, silicic acid.

Efficacy and Potency of 1-O-alkyl Glycerol Phosphate Prodrugs

The lipid derivative prodrugs of the invention, preferably 1-O-alkyl-sn-glycero-3-phosphate prodrugs, have advantageous pharmacological properties in comparison to the non-derivatized drugs.

The efficacy of the lipid prodrugs of the invention was demonstrated in tests carried out both in vitro and in vivo. 1-O-octadecyl-sn-glycero-3-phospho-3'-deoxy, 3'-azidothymidine(AZT) was used in oral absorption studies. This compound has an 18-carbon alkyl ether at position 1 of glycerol; the hydroxyl at position 2 of glycerol is open, and position 3 is linked by a phosphodiester bond to 3'-deoxy, 3'-azidothymidine(AZT)-5'-monophosphate. 1-O-octadecyl-sn-glycero-3-phospho-AZT does not require any metabolic conversions for absorption and appears to be absorbed directly from the gastrointestinal tract. It is not subject to deacylation by lysophospholipases in the gut because of the ether bond at position 1 of glycerol. Its metabolism is not known but it is hypothesized that the compound is metabolized by cellular enzymes and phosphodiesterases releasing 3'-deoxy, 3'-azidothymidine(AZT) or AZT-MP inside the cell.

The batyl alcohol derivative of AZT-monophosphate was evaluated in vivo for oral bioavailability in pharmacokinetic tests as described in Example 12 for which the results are shown in FIGS. 1–14. To interpret the results, it should be understood that free AZT is available orally but has an exceedingly short physiological half-life of about 30–60 min. In this study, the tissue level of the batyl-derivative AZT prodrug after oral administration was compared to the level of free AZT after intraperitoneal administration by noting the area under the curve (AUC) as the dose level in the tissue integrated over time. Notably, the AUC of AZT in plasma after oral administration of the lipid prodrug was 1.38 times greater than that of free AZT administered intraperitoneally, demonstrating clearly the anticipated advantage of this novel method of administration in maintaining the drug level in the plasma for a longer period of time. 1-O-octadecyl-sn-glycero-3-phospho-[$^3$H]AZT was demonstrated in the plasma by lipid extraction and thin layer radiochromatography. Significant amounts of free [$^3$H]AZT were not found until 12 hours following oral administration.

Figure 15:
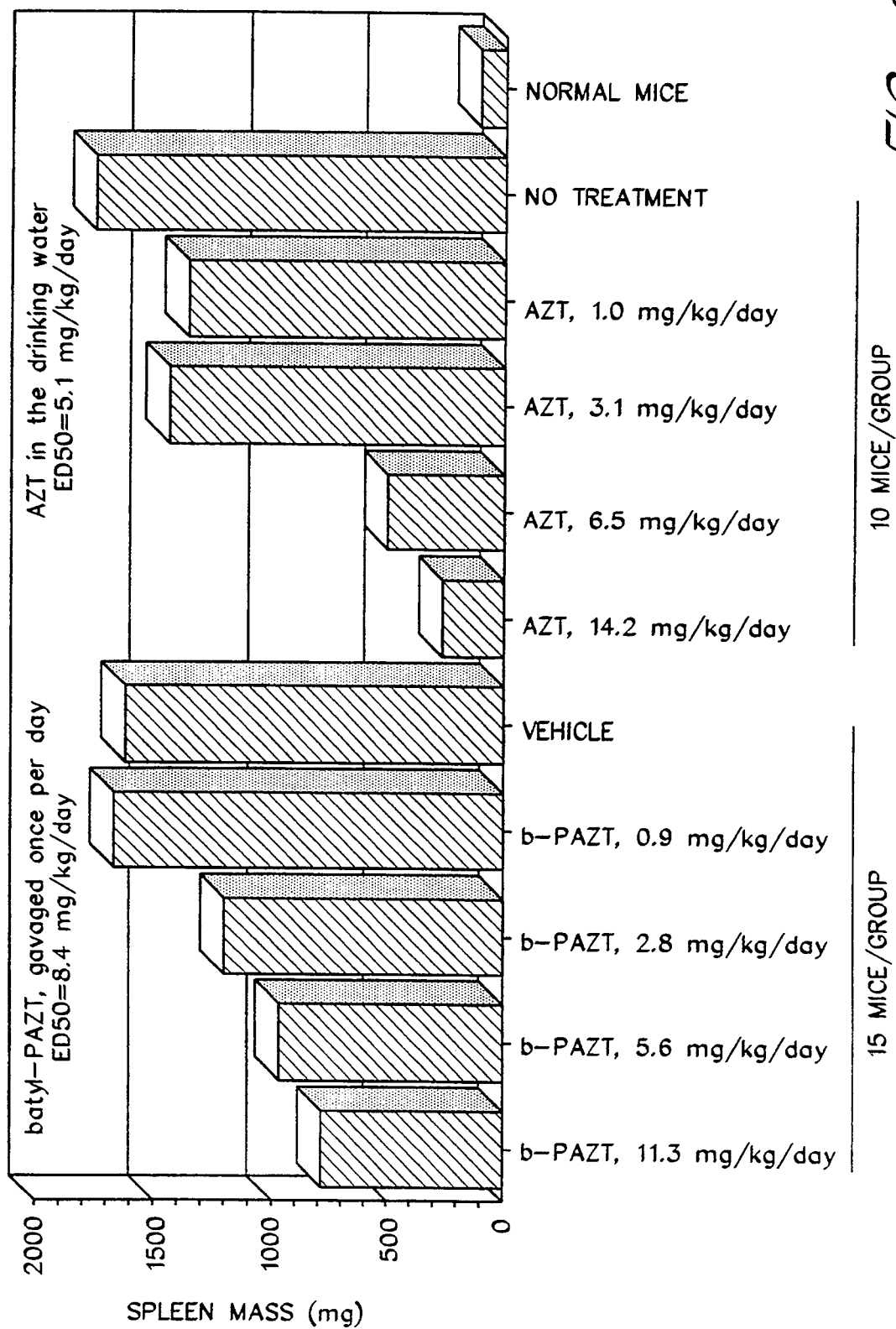
FIG. 15 is a graph showing the effect of batyl-P-AZT on spleen weight in Rauscher leukemia virus-infected mice after a single daily oral administration.
Figure 16A:
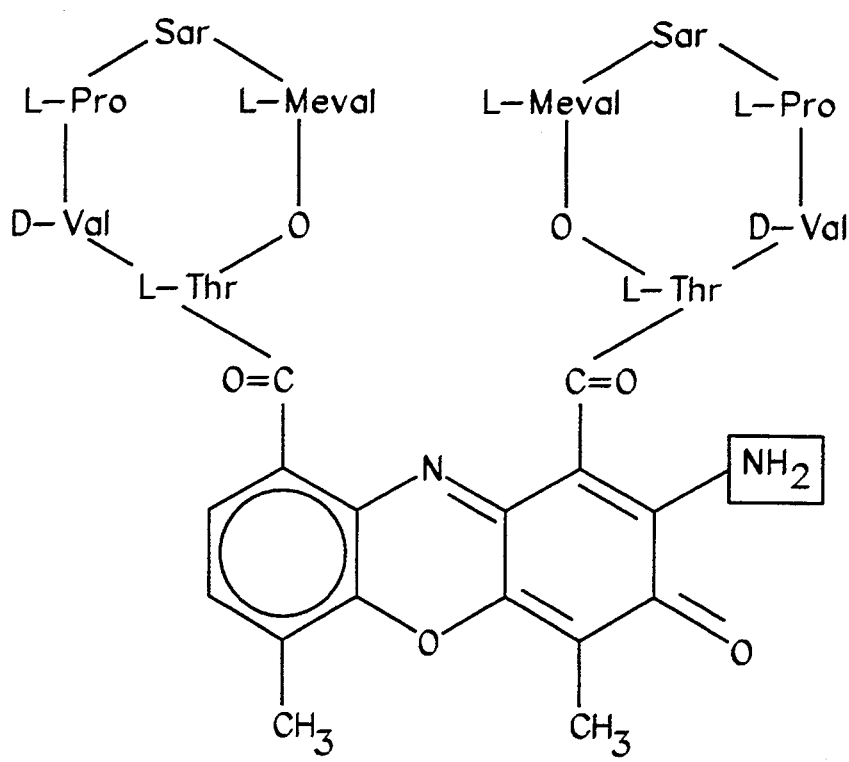
FIGS. 16–20 show the chemical structures of several classes of drugs from which orally bioavailable prodrugs can be prepared by attaching a lipid moiety to an available functional group according to the methods of the invention. Available groups are boxed; dashed boxes = weak acids.
Figure 16B:
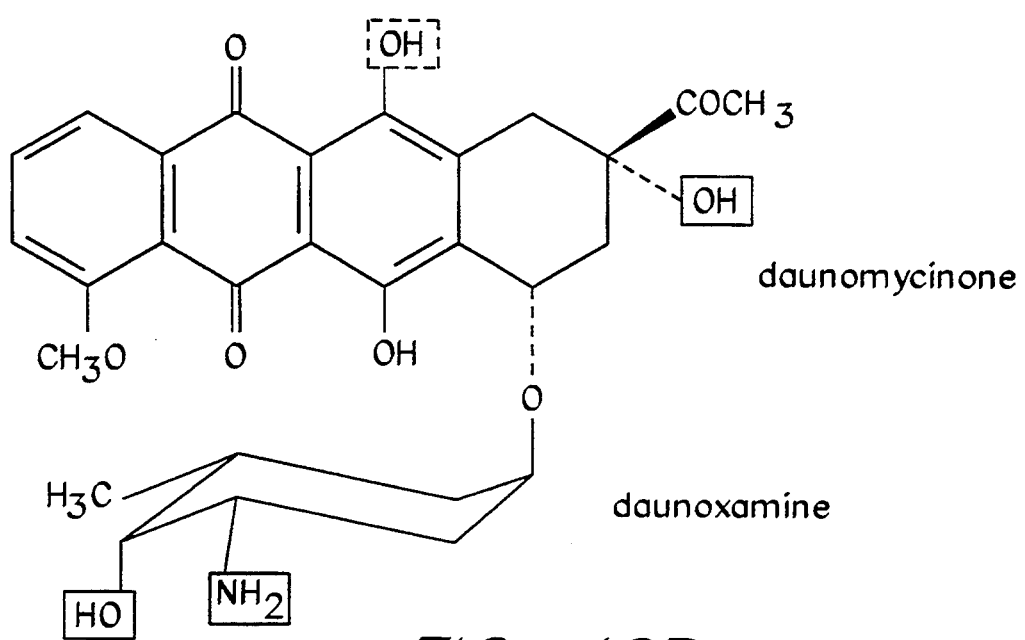
Figure 16C:
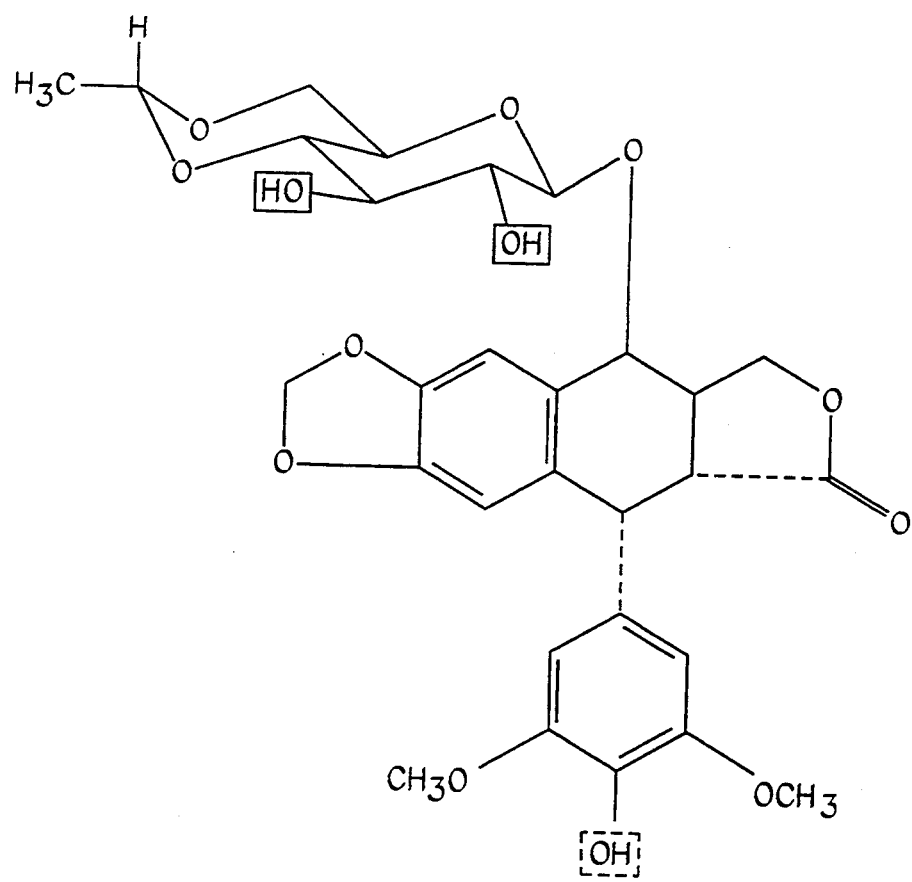
Figure 16D:
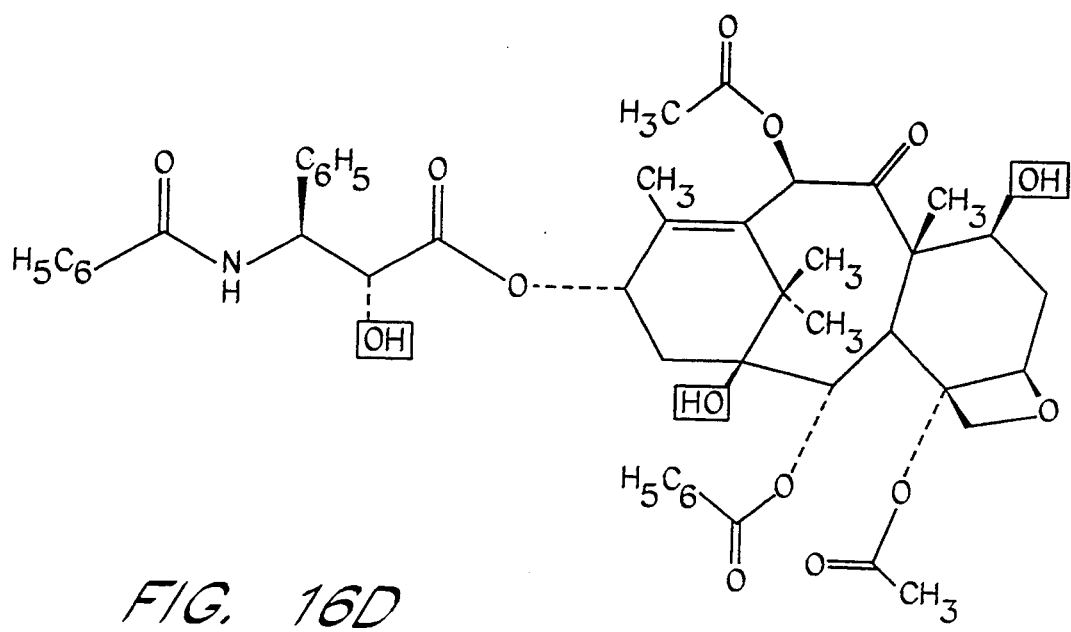
Figure 16E:
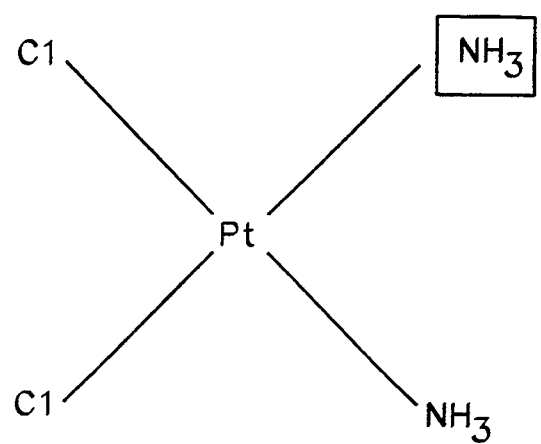
Figure 17A:
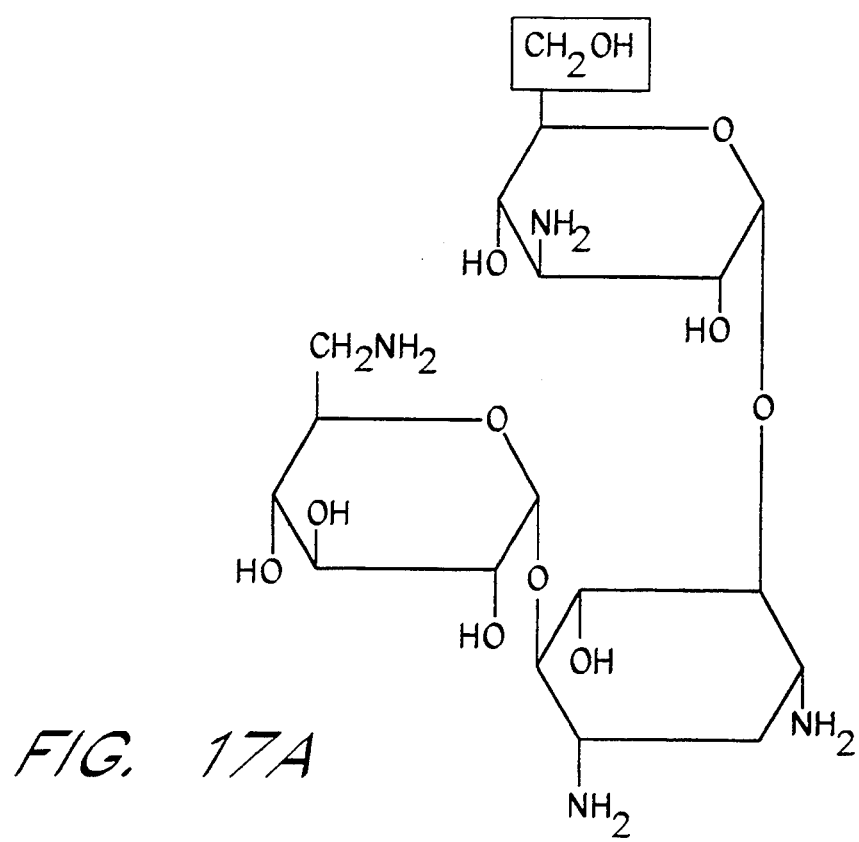
Figure 17B:
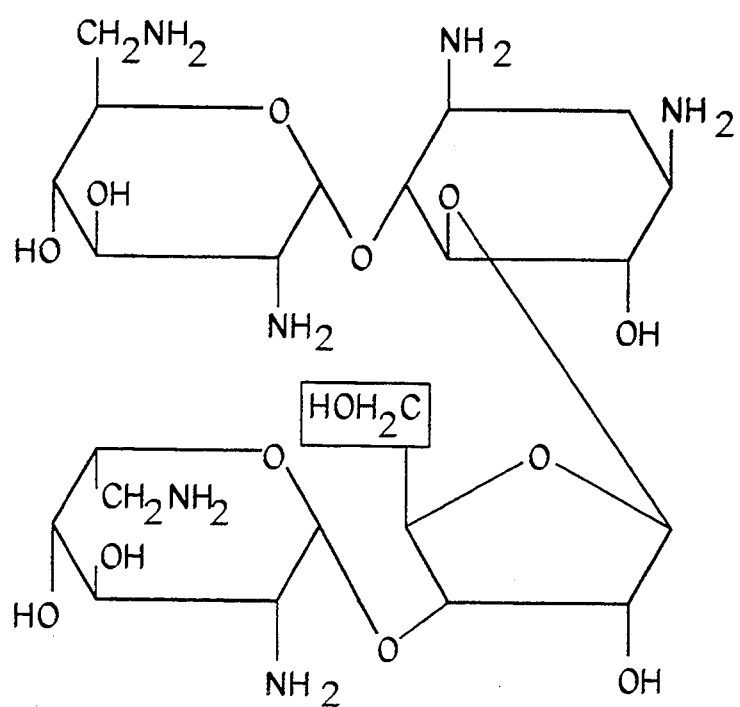
Figure 17C:
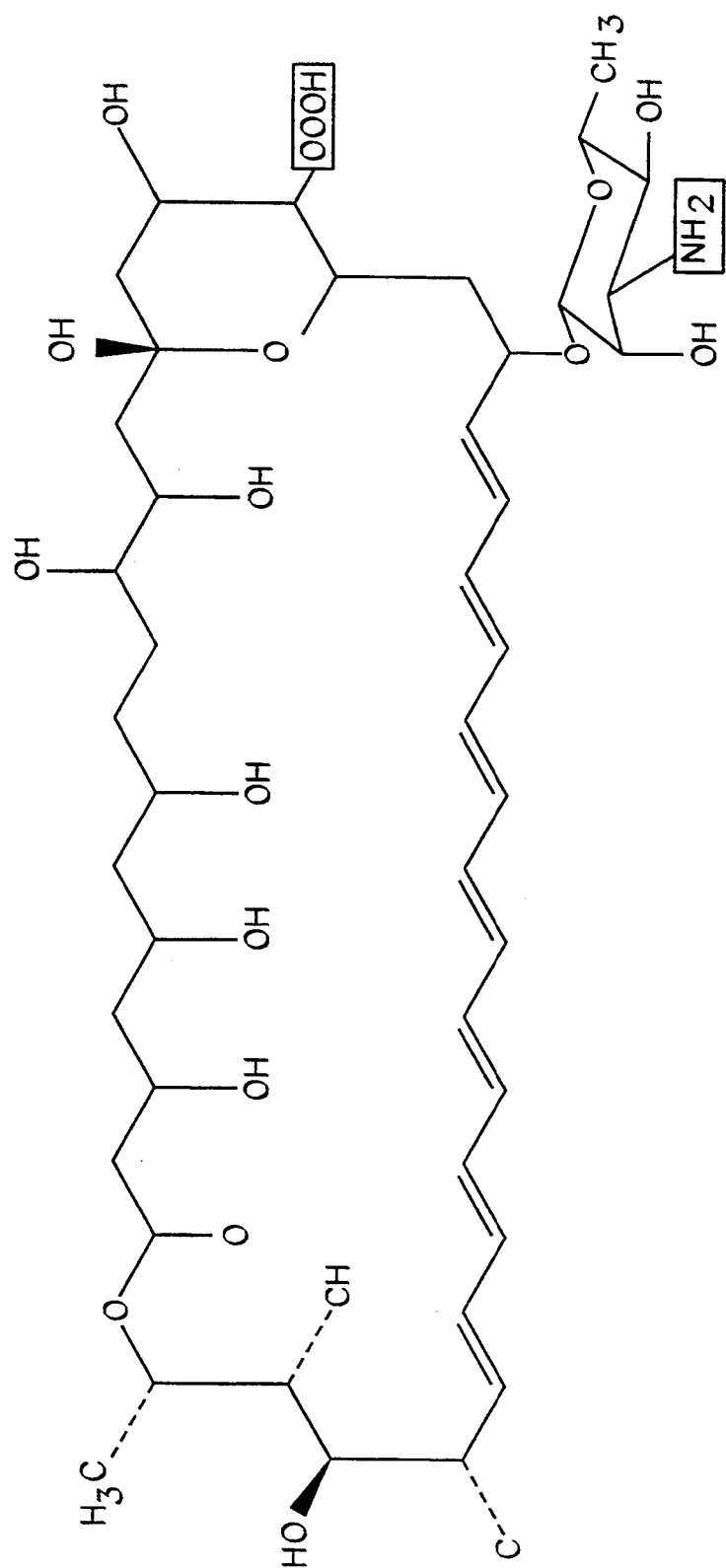
Figure 18A:
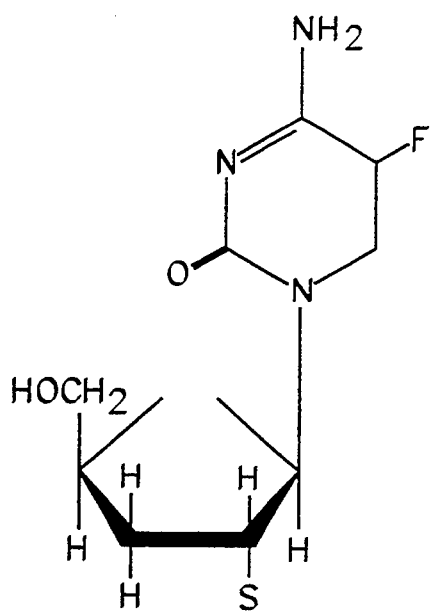
Figure 18B:
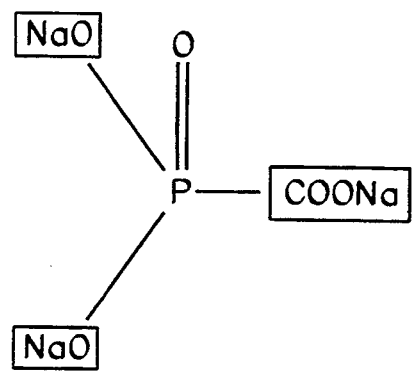
Figure 18C:
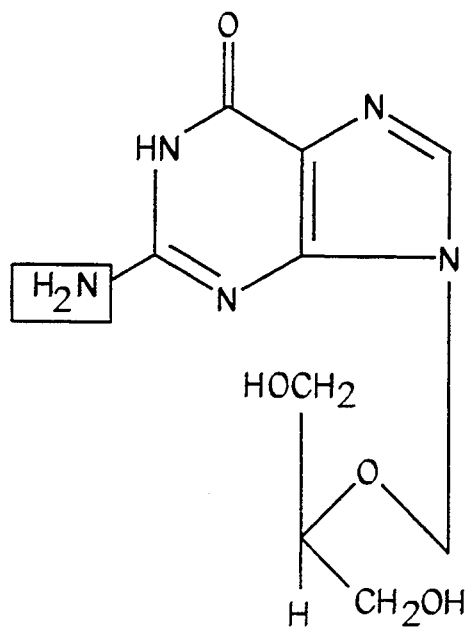
Figure 19A:
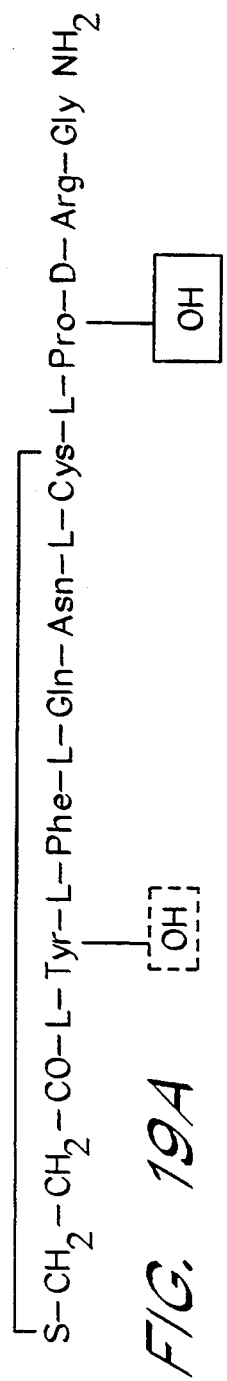
Figure 19B:
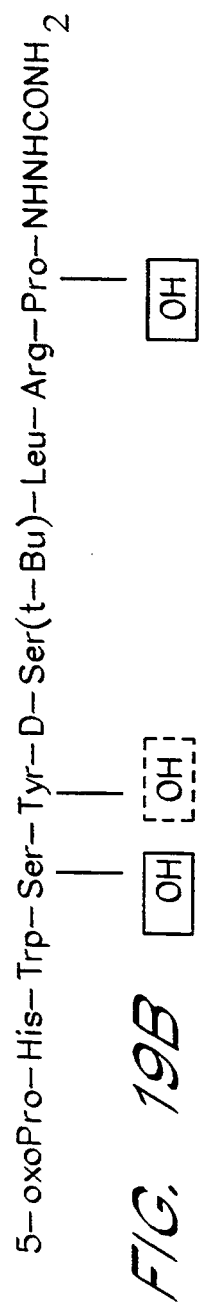
Figure 19C:
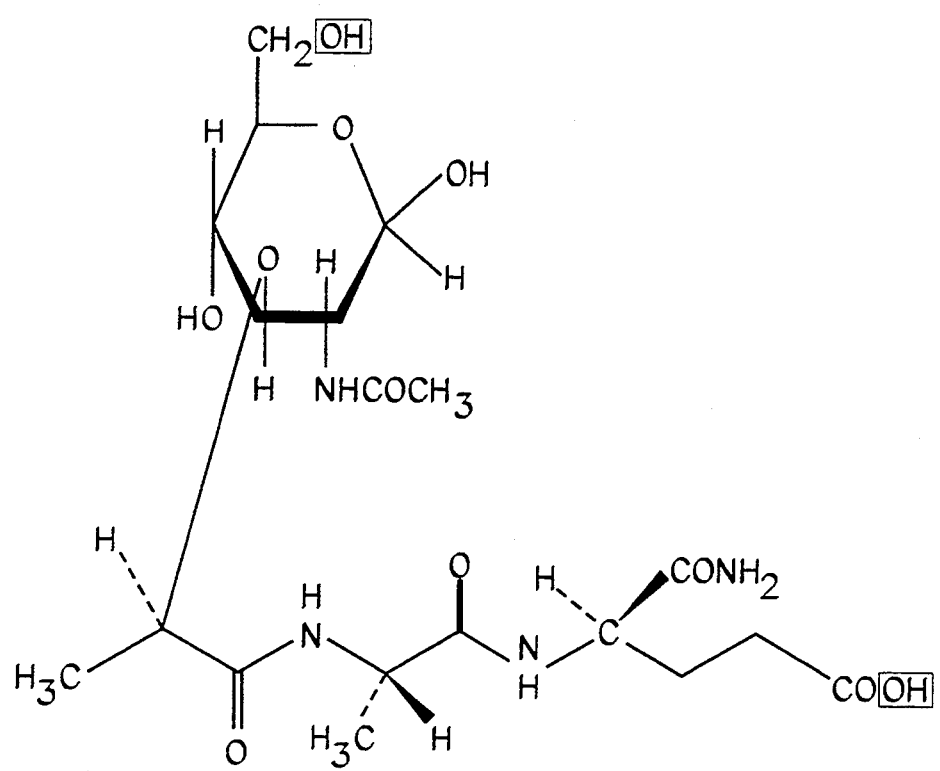
Figure 20A:
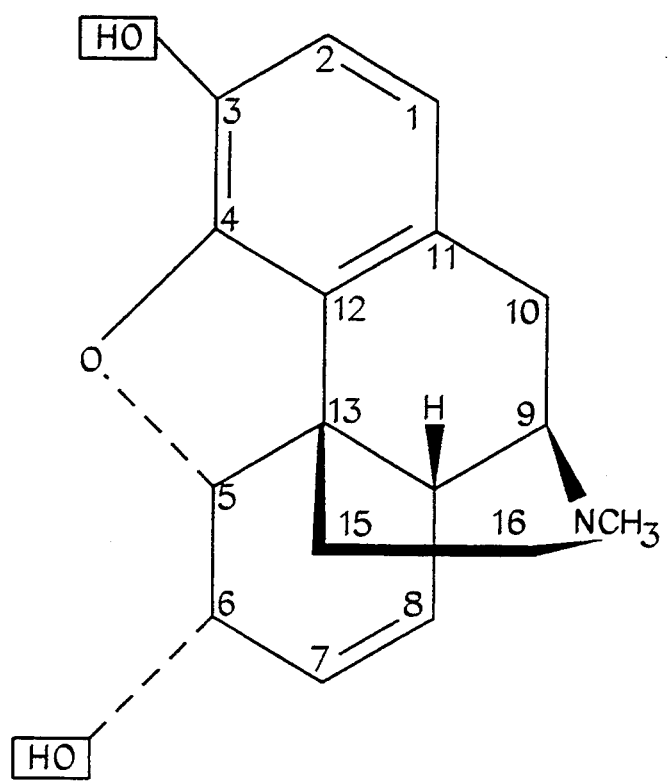
Figure 20B:
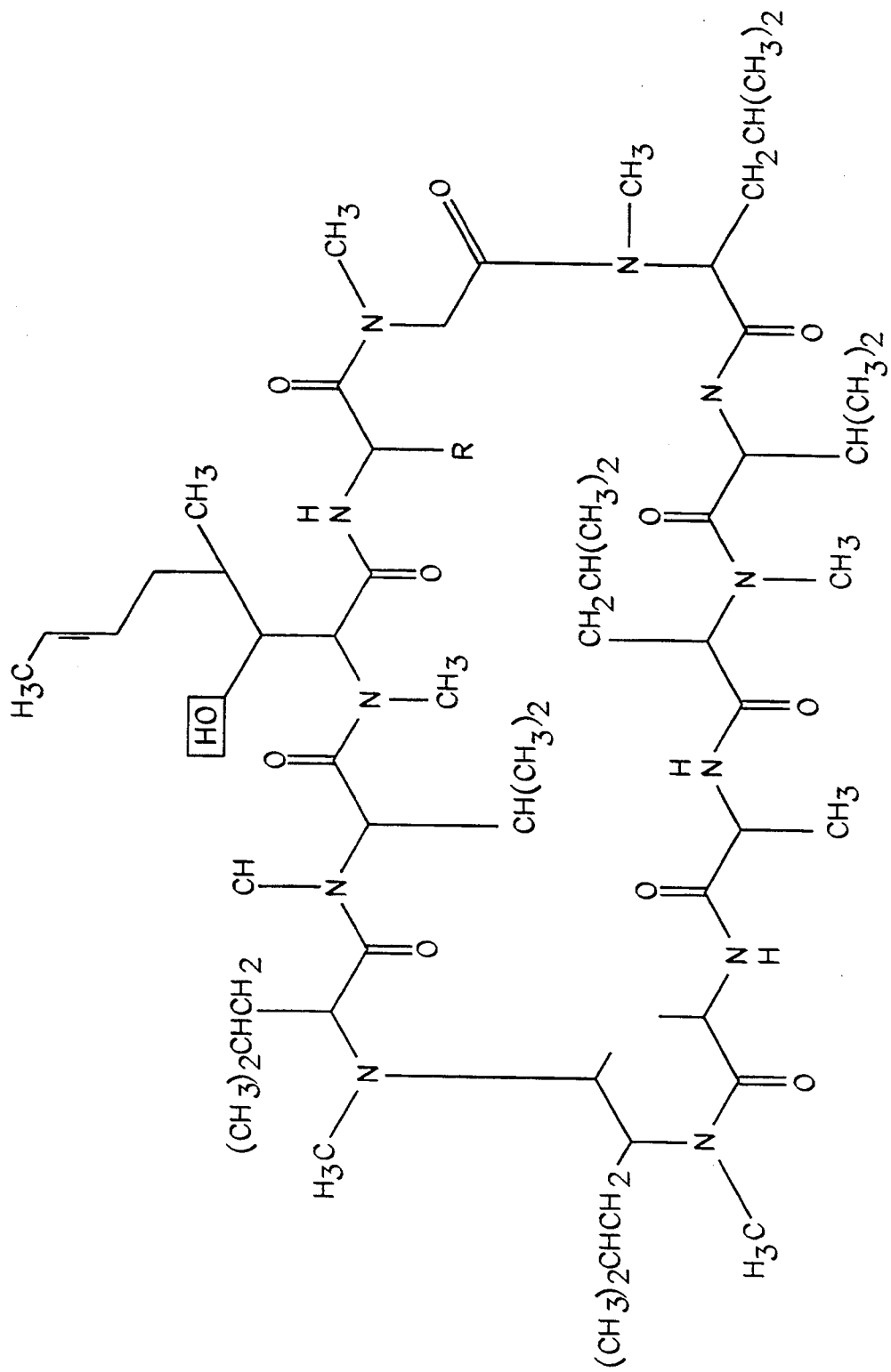

The in vivo study as described in Example 15 demonstrates that a 1-O-alkyl-sn-glycero-3-phosphate drug derivative has the same pharmacological efficacy as that of the non-derivatized agent. It further demonstrates that oral dosing with the batyl-P derivative can allow more convenient and effective administration of AZT. 1-O-batyl-sn-glycero-3-phospho-AZT was compared to free AZT in treating mice infected with Rauscher murine leukemia virus (RLV). RLV is a murine retrovirus, and RLV-infected mice are useful as a model system for evaluating therapeutic effectiveness of candidate anti-AIDS drugs against retrovirus induced disease in vivo. RLV infects splenocytes and the infected animals exhibit massive splenomegaly. Effective antiviral agents inhibit the splenomegaly, and a reduction in organ weight correlates with the elimination of virus (Ruprecht, R., et al., Nature 323:467–469 (1986)). Because AZT has a short physiological half-life, the most effective mode of AZT therapy should be continuous oral administration. The closest practical approach to optimum administration is the intake of AZT in drinking water. Oral administration of batyl-P-AZT on a once a day regimen of gavage proved to be as effective, in comparable doses, as virtually continuous free AZT administration, as determined by inhibition of splenomegaly in the infected mice (FIG. 15).

In in vitro studies, 1-O-octadecyl-sn-glycero-3-phospho-AZT had an $IC_{50}$ ranging from 0.4 to 1.1 $\mu M$ in HIV-infected HT4-6C cells. The anti-HIV activity of the sn-3 isomer and the racemic compound was identical.

Therapeutic Use of the Lipid Derivatives

The dosage of 1-O-alkyl glycerol phosphate prodrugs for a mammal, including a human, may vary depending upon the extent and severity of the condition that is treated and the activity of the administered compound. The dosage of the lipid prodrug is determined by reference to the recommended dosages of the active agent, bearing in mind that, in selecting the appropriate dosage in any specific case, consideration must be given to the patient's weight, general health, metabolism, age and other factors which influence response to the drug. Dosage levels for most commercially available therapeutic agents, as well as many agents that are being clinically investigated, are well established. For example, the dosage of 5-amino-4-imidazole carboxamide ribonucleoside (AICA-riboside) is reported to be from 0.1 to 500 mg/kg/day, preferably from about 15 to 200 mg/kg/day. The dosage of 1-O-octadecyl-sn-glycero-3-P-AZT, for example, can be from about 1 to 100 mg/kg/day, preferably 10 mg/kg/day.

Formulations for oral ingestion are in the form of tablets, capsules, pills, ampoules of powdered active agent, or oily or aqueous suspensions or solutions. Tablets or other non-liquid oral compositions may contain acceptable excipients, vehicles, diluents, fragrances, or flavors known to the art for the manufacture of pharmaceutical compositions, to make the medication palatable or pleasing to use. The formulation can therefore include diluents, such as lactose or calcium carbonate; binding agents such as gelatin or starch; and one or more agents selected from the group consisting of sweetening agents, flavoring agents, coloring or preserving agents to provide a palatable preparation. Moreover, such oral preparations may be coated by known techniques to further delay disintegration and absorption in the intestinal tract.

Aqueous suspensions may contain the active ingredient in admixture with pharmacologically acceptable excipients, comprising suspending agents, such as methyl cellulose; and wetting agents, such as lecithin or long-chain fatty alcohols. The aqueous suspensions may also contain preservatives, coloring agents, flavoring agents and sweetening agents in accordance with industry standards. The preparations may further comprise antioxidants, such as ascorbic acid or tocopherol, and preservatives, such as p-hydroxybenzoic acid esters.

The present invention is described below in detail using the following examples, but the chemical reactions described are disclosed in terms of their general application to the preparation of the lipid prodrugs of the invention. Occasionally, the reaction may not be applicable as described to each compound included within the disclosed scope of the invention. The compounds for which this occurs will be readily recognized by those skilled in the art. In all such cases, either the reactions can be successfully performed by conventional modifications known to those skilled in the art, e.g., by appropriate protection of interfering groups, by changing to alternative conventional reagents, or by routine modification of reaction conditions. Alternatively, other reactions disclosed herein or otherwise conventional will be applicable to the preparation of the corresponding compounds of the invention. In all preparative methods, all starting materials are known or readily preparable from known starting materials; all temperatures are set forth uncorrected in degrees Celsius; and, unless otherwise indicated, all parts and percentages are by weight.

It is believed that one skilled in the art can, using the preceding description, utilize the invention to its fullest extent. The following preferred embodiments are, therefore, to be construed as merely illustrative and not limitative for the remainder of the disclosure in any way whatsoever.

EXAMPLE 1

Preparation of Lipid Moieties Used in the Coupling Procedures

Synthesis of 1-O-alkyl-2-benzyl-sn-glycero-3-phosphatidic acid (1)

To a vigorously stirred solution of 1-octadecyl-2-benzyl glycerol (Bachem, Inc., Basel, Switzerland), hereinafter referred to as OBG, a mixture of pyridine, triethylamine and tetrahydrofuran (THF) was added. Neat phosphorous oxychloride, $POCl_3$, was added dropwise while maintaining the temperature between $-5°$ to $5°$ C. The reaction mixture was stirred for 90 minutes at a temperature of $4°$ C. The precipitated triethylamine hydrochloride was filtered and the residue treated with toluene at least twice ($2 \times 10$ ml) and the solvent removed under reduced pressure. The resulting oil was converted to the ammonium salt upon careful addition of methanolic ammonium hydroxide. The yield was 55%, and the target compound was a white to pale yellow solid.

N-tritylethanolamine (2)

A mixture of ethanolamine, trityl chloride and pyridine was refluxed for 15 h. Water was added slowly to the cooled reaction and the precipitate collected by filtration. The crude product recrystallized from a 1:1 mixture of ethanol and water.

N-trityl-O-(1-O-octadecyl-2-benzyl-sn-glyero-3-phosphoryl)-ethanolamine

A mixture of 1, 2, and trisopropylbenzenesulfonyl chloride in pyridine was stirred at a temperature of $25°$ C. for a period of 24 h. The desired compound was extracted from the reaction mixture and detritylation was carried out by methods familiar to those skilled in the art.

EXAMPLE 2

Coupling of 1-O-alkyl Glycerol to a Phosphorylated Drug Derivative

I. Synthesis of Batyl-P-Acyclovir (Batyl-P-ACV):

Ia Preparation From ACV monophosphate and batyl alcohol

Acyclovir was phosphorylated by addition of phosphorous oxychloride $POCl_3$. After 1–2 h at 0° C. acyclovir was extracted with ether as the phosphoryl dichloride. A 2N NaOH solution was added to an aqueous solution of the dichloride to bring the pH to about 9 to 10, converting the compound to the disodium form. Chromatography on Dowex 50 converted the disodium salt to acyclovir monophosphate. A solution of acyclovir monophosphate as its salt, such as tributylamine or trioctylamine, in pyridine was treated with batyl alcohol followed by triisopropylbenzenesulfonyl chloride (TIPS) at a temperature of 45° C. for a period of 28 h. The dark-colored solution was treated with water, followed by toluene, and the resulting solution was concentrated under reduced pressure. The crude product was purified by ion exchange chromatography followed by silica column chromatography to obtain the desired compound as a white chloroform-soluble powder in a yield of 50% with a purity >95%.

II. Synthesis of Batyl-p-ara-C:

IIa: Preparation from ara-C monophosphate and batyl alcohol

A solution of cytosine arabinoside(ara-C)-5'-monophosphate (Sigma, St. Louis, Mo.), batyl alcohol, and triisopropylbenzenesulfonyl chloride (TIPS) in pyridine was allowed to stir at a temperature of 45° C. over a period of 25 h. Water was added to the reaction mixture followed by toluene and the solvents removed under reduced pressure. The crude product was chromatographed on silica gel to afford the desired compound.

IIb: Preparation from 1-O-alkyl-2-benzyl-glycerol (OBG)

Alternatively, batyl-P-ara-C can be prepared starting from OBG as delineated in the preparation of 1 in Example 1 in which OBG can be used to couple with ara-C-monophosphate.

IIc: Preparation from 1-O-stearoyl glycerol

A solution of ara-C-monophosphate, 1-O-stearoyl-glycerol and triisopropylbenzenesulfonyl chloride (TIPS) in pyridine was allowed to stir at a temperature of 45° C. over a period of 25 h. Water was added to the reaction mixture followed by toulene and the solvents removed under reduced pressure. The crude product was purified by silica chromatography to afford the desired compound with the desired purity.

EXAMPLE 3

Coupling of Drugs Having a Free Carboxyl Group to the Amino Group of a Monoglyceride Phosphorylethanolamine Preparation of the Batyl Derivative of Cefazolin 1-O-octadecyl-sn-glycero-3-phosphoethanolamine (1 mmol) and cefazolin (1.2 mmol, 3[[(5-methyl-1.3.4-thiadiazol-2-yl)thio]-8-oxo-7[[(1H-tetrazol-1-yl) acetyl]amino]5-thia-1-azabicyclo[4.2.0]oct-2-ene-2-carboxylic acid) were dissolved in pyridine followed by N,N-dicyclohexylcarbodiimide (3 mmol, DCC). The reaction mixture was stirred for 24 h at 10° C. The reaction was stopped by the addition of cold water and the solvents were evaporated and the product was purified by preparative thin layer chromatography.

The following compounds were similarly coupled to 1-O-octadecyl-sn-glycero-phosphoethanolamine by using the above procedure.

3a: ceftazidime {1-[[7-[[(2-amino-4-thiazolyl)[1-carboxy-1-methylethyoxy)imino]acetyl]amino]-2-carboxy-8-oxo-5-thia-1-azabicyclo[4.2.0]]oct-2-en-3-yl]methyl]-Pyridinium hydroxide}, 3b: ceftiaxone {7-[[2-amino-4-thiazolyl)(methoxyimino)acetyl]amino]8-oxo-3-[[1,2,5,6-tetrahydro-2-methyl-5,6-dioxo-1,2,4-triazin-3-yl)thio]methyl]-5-thia-1-azabicyclo[4.2.0]oct-2-ene-2-carboxylic acid}; and 3c: piperacillin {[[[[(4-ethyl-2,3-dioxo-1-piperazinyl)-carbonyl]amino]phenylacetyl]amino]-3,3-dimethyl-7-oxo-4-thia-1-azabicyclo[3.2.0]heptane-2-carboxylic acid}

EXAMPLE 4

Coupling Drugs Containing a Free Amino Group to a Monoglyceride Phosphate Through an Aliphatic Chain Linker Preparation of 1-O-alkyl-sn-glycero phosphate derivatives of ceftazolin 4a: Hydroxycarboxylic acid linker Hydroxybutyric acid sodium salt (0.5 mol, Aldrich) was dissolved in methanol and dry HCl was passed to convert the acid to its methyl ester. Methanol was evaporated and the dry methyl ester linking compound was coupled to 1-O-alkyl-sn-glycero-3-phosphate by using N,N'-dicyclohexyl carbodiimide (DCC) as a coupling agent. The resulting compound was subjected to a base-catalyzed methanolysis by using 0.5N methanolic sodium hydroxide and the free acid derivative was again coupled to various drugs containing free amino groups, such as, for example, the methyl ester of ceftazidime, or sulfmethazine as described above. The protective ester group was removed frm the drug by treatment with base.

4b: Dihydroxyl linker

In another embodiment, the carboxylic acid group of the linker was reduced to an alcohol group (after coupling to 1-O-alkyl-sn-glycero-3-phosphate) to couple to free drugs having a free acid moiety.

EXAMPLE 5

1-O-Octadecyl-2-benzyl-sn-glycero-3-phosphoryl Ara-C(3) and 1-O-Octadecyl-sn-glycero-3-phosphoryl Ara-C(4) (Batyl-P-Ara-C)

5a: A solution of 1-O-alkyl-2-benzyl-sn-glycero-3-phosphatidic acid (1) and ara-C in pyridine was treated with TIPS at a temperature of 40° C. over a period of 24 h. The reaction was stopped by addition of water and the solvent evaporated under reduced pressure. The crude product purified by chromatography to afford (3). Debenzylation of 3 using standard procedures afforded the desired compound 4.

5b: Alternative preparation of compound 3 and 4 involved the coupling of OBG and ara-C monophosphate using pyridine as the solvent and TIPS as the coupling agent. Purification of 3 and debenzylation was effected using the standard procedures to afford 4.

5c: 2'-ara-fluoro-2-chlorodeoxyadenosine

5d: 5-fluorouridine

5e: 6-mercaptopurine riboside

5f: 3'-thia-dideoxycytidine

5g: 3'-thia-5-fluoro-dideoxycytidine

EXAMPLE 6

Synthesis of Batyl-P-5-amino-4-imidazole Carboximide Ribonucleoside (Batyl-P-AICA Riboside)

A solution of 1-O-alkyl-2-benzyl-sn-glycero-3-phosphatidic acid (1) and AICA riboside in pyridine containing TIPS was reacted at a temperature of 40° C. over a period of 24 h. The reaction was stopped by addition of water and the solvents evaporated under reduced pressure. The crude product purified by chromatography and debenzylated using standard procedures to afford the batyl-P-AICA-riboside. Alternatively, batyl alcohol and AICA-riboside monophosphate in pyridine, in the presence of TIPS, was stirred at a temperature of 50° C. over a period of 25 h. The reaction was worked up as before to afford batyl-P-AICA riboside.

EXAMPLE 7

Synthesis of 1-O-octadecyl-glycero-rac-3-phospho-5'-(3'-deoxy, 3'-azido)thymidine:

Dry 1-O-octadecyl-rac-3-glycerol (batyl alcohol, 250 mg), 3'-azido-3'-deoxythymidine monophosphate sodium salt (0.725 gm) and 2,4,6,-triisopropylbenzenesulfonyl chloride (TPS, 1.219 gm) were mixed in dry pyridine and stirred overnight under nitrogen. Chloroform (50 ml) was added and the reaction mixture was washed twice with cold 0.2N HCl and 0.2N sodium bicarbonate. The organic phase was removed in vacuo with a rotary evaporator and the product was crystallized at −20° C. from 20 ml of chloroform/acetone (12:8 by volume). The final purification of the compound was done by preparative thin layer chromatography using 500 micron layers of silica gel G developed with chloroform/methanol/concentrated ammonia/water (70/30/1/1 by volume).

EXAMPLE 8

Synthesis of Batyl-Phosphonoformate

A quantity of 0.9 grams of racemic batyl alcohol (1-O-octadecyl-2,3-glycerol, Sigma Chemical, St. Louis, Mo.), 2.6 grams of triisopropylbenzenesulfonyl chloride (TPS, Aldrich, Milwaukee, Wis.) and 0.16 grams of phosphonoformate, acid form, were reacted in 15 ml of dry pyridine at room temperature under nitrogen. The reaction was monitored at half hour intervals by thin layer chromatography and was judged to be complete at about 24 hours. The reaction was stopped by the addition of 10 ml of chloroform/methanol/water (1/2/0.8 by volume). The organic (lower) phase was separated by further addition of 2 ml of chloroform and 2 ml of water. The organic phase was removed and evaporated in vacuo and the product was obtained as a white powder. The crude product was dissolved in a small volume of chloroform/methanol (1/1 by volume) and subjected to preparative thin layer chromatography using 0.5 mm layer of chloroform/methanol/concentrated ammonia/water (70/30/1/1). Two phosphonoformate (PFA)-containing spots were visualized, scraped and extracted with chloroform/methanol/water. The two compounds are referred to as batyl-PFA, top and bottom, respectively.

EXAMPLE 9

Coupling 1-O-alkyl-sn-glycerophosphatidic Acid to the Amino Group of a Peptide 1-O-alkyl-2-benzyl-sn-glycero-3-phosphatidic acid, prepared as in Example 1 above, was partitioned between chloroform:methanol (2:1 (v/v); 200 ml) and cold 1N HCl (50 ml). The aqueous layer was re-extracted with chloroform methanol (2:1 (v/v); 100 ml). The combined organic phase was evaporated and dried under vacuum over $P_2O_5$. The resulting free phosphatidic acid was dissolved in a mixture of DMF (2 ml) and pyridine (2 ml) and to the solution was added the appropriate peptide having a free amino group (1 mmol) followed by N,N'-dicyclohexylcarbodiimide (DCC; Aldrich Chemical Co. Milwaukee Wis., MW: 206, 620 mg, 3 mmol). The reaction mixture was stirred for 24 hours at room temperature. The solvents were evaporated and the product was purified by flash chromatography over silica gel column (2.5×50 cm) using a linear gradient of 0 to 50% methanol in chloroform. Fractions containing the desired product as indicated by TLC and HPLC were pooled and evaporated. The product was further purified, if necessary, by preparative HPLC or by crystallization. Debenzylation of the compound offered 1-O-alkyl-sn-glycero-3-phosphoramidate.

EXAMPLE 10

Coupling 1-O-alkyl-2-benzyl-3-phosphoethanolamine to the Amino Group of a Therapeutic Peptide Using Succinate as a Linking Group A solution of 1-O-alkyl-2-benzyl-3-phosphatidic acid and ethanolamine in pyridine was treated with N,N'-dicyclohexylcarbodiimide and the mixture was to stir at room temperature for a period of 24 h. The solvents were evaporated and the product purified by chromatogrphy. Fractions containing the desired product was pooled and evaporated. The 1-O-alkyl-2-benzyl-3-phosphoethanolamine was next treated with succinic anhydride to afford the hemisuccinate of 1-O-alkyl-2-benzyl-3-phosphoethanolamine. The free carboxyl group of the hemisuccinate was coupled to the N-terminal amino group of a HiV protease inhibitor[D-Phe]-[D-α-napthylalanine]-pipecolic acid -[α-OH-Leu]-Val amide (VST 7140) or a peptide such as VST 7194 or a renin inhibitor, enalkiren (A64662).

Preparation of DPPE-succinio acid

The lipid-linker material 1,2-dipalmitoyl-sn-glycero-3-phospho-O-(N-succinyl)-ethanolamine (DPPE-Suc) was prepared by reacting one equivalent of 1,2-dipalmitoyl-sn-glycero-3-phosphatidylethanolamine (DPPE; Avanti Polar Lipids, Birmingham, Ala.) and one equivalent of triethylamine with three equivalents of succinic anhydride (Sigma Chemical Co., St. Louis, Mo.) in chloroform. The reaction was stirred at room temperature under dry nitrogen atmosphere for 16 hours. Upon completion of the reaction, the product material was purified by silica gel chromatography using a solvent gradient of 100% chloroform to 15% methanol in chloroform.

Lipid-peptide derivatives

The lipid-derivatized polypeptide HIV protease inhibitor designated VST-7172 was prepared by reacting one equivalent of DPPE-Suc in dimethylformamide DMF) with one equivalent of VST-7140 peptide containing a free amine function at the N-terminal and 3 equivalents of N,N'-dicyclohexylcarbodiimide (DCC) in dichloromethane. The reaction was stirred for 24 hours at room temperature under dry conditions, after which time, the product was purified by silica gel chromatography using a solvent gradient of increasing methanol in chloroform.

The C-terminally derivatized HIV protease inhibitor VST-7196 from iBOC-[L-Phe]-[O-β-Nal]-[α-OH-Leu]-Val-COOH (VST 7194) was prepared by reacting one equivalent of DPPE and the 7194 peptide in DMF with two equivalents each of DCC and 1-hydroxybenzotriazole. The reaction was stirred for 16 hours at room temperature under dry conditions, and the target compound was then purified by preparative thin layer chromatography using a solvent system of 85:10:5 chloroform:methanol:acetic acid on 1000 μm 20×20 cm si0-lica gel GF plates from Analtech Inc. (Newark, Del.).

The purified lipid derivatives were subsequently characterized by HPLC, amino acid analysis, fast atom bombardment mass spectrometry and gas chromatography fatty acid ratio analysis.

EXAMPLE 11

Coupling 1-O-alkyl-sn-glyoero-phosphatidic Acid to the Hydroxy Group of a Peptide 1-O-alkyl-2-benzyl-sn-glycero-3-phosphatidic acid (1 mmol) prepared as above was dissolved in a mixture of DMF (2 ml) and pyridine (2 ml) and to the solution were added the appropriate peptide having a free hydroxyl group (1 mmol) followed by DCC (620 mg, 3 mmol). The reaction was carried out and the product was isolated as described in Example 1.

The condensation of the phosphatidic acid and the hydroxyl group of a peptide was also conveniently carried out by using 2,4,6-triisopropylbenzenesulfonyl chloride (TPS-Cl; Aldrich Chemical Co., Milwaukee, Wis.; MW: 302.86; 758 mg, 2.5 mmol) as a coupling agent in place of DCC. Debenzylation was effected as in Example 9.

EXAMPLE 12

Coupling a Peptide Containing a Free Carboxyl Group to the Amino Group of a Monoalkyl Phosphorylethanolamine A mixture of the appropriate peptide (1 mmol), and 1-O-octadecyl-sn-glycero-3-phosphoethanolamine (1 mmol) was dissolved in pyridine (5 ml) and DCC (3 mmol) followed by 1-hydroxybenzotriazole (HOBt; Aldrich Chemical Co., HOBt, MW: 153; 450 mg, 3 mmol) was added. The reaction mixture was stirred for 24 hours at room temperature and the product was purified by silica gel chromatography as described in Example 1 followed by debenzylation as in Example 1.

EXAMPLE 13

Synthesis of Lipid Derivative of a Taxol Side Chain

Synthesis of β-(Benzoylamino)-α-((1,2-diacyl-sn-glycero-3-phospho)-benzenepropanoate, ester (1).

A solution of 1,2-diacyl-sn-glycero phosphate such as 1,2-dipalmitoyl-sn-glycero phosphatidic acid (0.5 mol, Genzyme) and β-(benzoylamino)-α-hydroxybenzenepropanoate ester either in an ethereal solvent like diethyl ether, tetrahydrofuran or a halogenated solvent like dichloromethane or chloroform was added DCC either neat or as a solution and allowed to stir for 2–25 h at a temperature of 4° C. Water was added to the reaction mixture and the solvents removed under reduced pressure. The crude product was chromatographed on silica gel to afford the desired compound.

Synthesis of β-(Benzoylamino)-α-((1-O-octadecyl-2-benzyl-sn-gylcero-3-phospho)-benzenepropanoate, ester (2).

A solution of 1-O-octadecyl-2-benzyl-sn-glycero-3-phosphatidic acid (0.1 mol), β-(benzoylamino)-α-hydroxybenzenepropanoate ester in pyridine or chloroform was stirred in the presence of DCC (0.4 mol) at a temperature of 4° C. for a period of 6 h. Water was added to the reaction mixture and the contents extracted with chloroform. The solvent was removed under reduced pressure and the crude product purified by chromatography to afford the benzenepropanoate ester.

EXAMPLE 14

Synthesis of β-amino Substituted Taxol Side Chain

Synthesis of β-Amino-α-(1-O-octadecyl-2-benzyl-sn-glycero-3-phospho)-benzenepropanoate ester.

A solution of 1-O-octadecyl-2-benzyl-sn-glycero-3-phosphatidic acid (0.1 mol), β-amino-α-hydroxybenzenepropanoate ester (0.1 mol) in chloroform or pyridine was added DCC (0.4 mol) and allowed to stir at a temperature of 4° C. for a period of 5 h. Water was added to the reaction mixture and the contents extracted with chloroform or other halogenated solvent. The solvent was removed under reduced pressure and the crude product purified by chromatography to afford the substituted ethanolamine of batylbenzyl phosphatidic acid.

EXAMPLE 15

Hydrolysis of Propanoate Esters of Lipid Derivatized Taxol Side Chain

Synthesis of β-(Benzoylamino)-α-((1,2-diacyl-sn-glycero-3-phospho)-benzenepropanoic acid (3).

The propanoate ester (0.1 mol) from (1) was hydrolyzed using sodium methoxide in methanol or sodium carbonate in methanol at a temperature of 5° C. for a period of 4 h to afford the desired compound which is ready for coupling with baccatin III or 10-deacetyl baccatin III.

Synthesis of β-(Benzoylamino)-α-(1-O-octadecyl-2-benzyl-sn-glycero-3-phospho)-benzenepropanoic acid.

To a solution of 2(0.1 mol) in methanol was added a solution of sodium methoxide in methanol and the resulting solution was stirred at a temperature of 5° C. for a period of 4 h. The reaction mixture was neutralized and the resulting solution concentrated under reduced pressure to afford the crude product. Purification by column chromatography gave the desired compound which is suitable for coupling with baccatin III or 10-deacetylbacatin.

EXAMPLE 16

Coupling of Lipid Derivative of Taxol Side Chain to Baccatin

A. Coupling of lipid derivative of phosophoethanolamine side chain to 10-deacetyl baccatin III.

To a solution of β-(benzoylamino)-α-(1,2-diacyl-sn-glycero-3-phospho)-benzenepropanoic acid (example 15) (0.1 mol) and 10-deacetylbaccatin III (0.1 mol) in chloroform was added DCC (0.4 mol) and allowed to stir at a temperature of 25° C. for a period of 7 h. Water was added to the reaction mixture and the contents extracted with chloroform. The organic layer was separated and the aqueous phase was extracted with chloroform. The combined organic layer was concentrated under reduced pressure and the crude product purified by chromatography to afford the 1,2-diacyl-sn-glycero-3-phosphoethanolamine derivative of taxol.

B. Coupling of batylbenzylphosphoethanolamine side chain to 10-deacetyl baccatin III.

To a solution of β-(benzoylamino)-α-(1-O-octadecyl-2-benzyl-sn-glycero-3-phospho)-benzenepropanoic acid (0.1 mol), 10-deacetyl baccatin III (0.1 mol) in chloroform was added DCC (0.4 mol) and allowed to stir at room temperature for a period of 10 h. Water was added to the reaction mixture and the contents extracted with chloroform. The organic layer was separated and the aqueous layer was extracted with chloroform. The combined organic layer was concentrated under reduced pressure and the crude product purified by chromatography to afford the batylbenzylphosphoethanolamine derivative of taxol.

In the preceding syntheses, proton NMR spectra were obtained with a General Electric QE-300 spectrometer, using tetramethylsilane as internal standard (key: s=singlet, d=doublet, t=triplet, q=quartet, dd=doublet of doublets, b=broad), UV spectra were recorded on Shimadzu UV-160, spectrophotometer. Fast atom bombardment mass spectra were determined by Mass Spectrometry Service Laboratory, University of Minnesota. Elemental analyses were determined by Galbraith Laboratories, Knoxville, Tenn. and Schwarzkopf Microanalytical Laboratory, N.Y. Melting points were obtained with a Fisher-Johns melting apparatus. Column chromatography was carried out on Merck silica gel 60 (70-230 mesh). Rf values were obtained with HPTLC Merck, Kieselgel 60 pre-coated plates, 10×10 cm. Anhydrous pyridine, 2,4,6-Triisopropylbenzenesulfonyl chloride (TPS), and 3'-azido-3'-deoxythymidine (AZT) were purchased from Aldrich Chemical Co., Milwaukee, Wis. Dimyristoylphosphatidic acid, disodium salt, was purchased from Avanti; batyl alcohol was obtained from Sigma Chemical, St. Louis, Mo. and 1-O-octadecyl, 2-benzylglycerol from Bachem Bioscience Inc., Philadelphia, Pa.

EXAMPLE 17

ORAL ADMINISTRATION OF 1-O-OCTADECYL-sn-GLYCERO-3-PHOSPHO-AZT-$^3$H

A quantity of 8 μmol of 1-O-octadecyl-sn-glycero-3-phospho-AST-$^3$H (spec. act. 5890 DPM/nmole) and 96.7 μmol of egg phosphatidyl choline (PC) was suspended in 1.0 ml of 250 mM acetate buffer, pH 5.5. The sample was sonicated at 55° C. for one hour. Drug concentration was determined by counting the final sonicate. 0.1 ml doses equivalent to 10 mg AZT/kg body weight were given orally to mice using a feeding tube.

After the indicated time, the mice were sacrificed and blood and tissues were collected. Plasma was collected from two mice, using an orbital bleed, and a third mouse was sacrificed for blood and organs. Plasma was processed as described below. Tissues were removed, rinsed in saline, blotted dry, and placed into scintillation vials for further processing. To liver samples, 3 ml of distilled H$_2$O was added before homogenization with a Polytron. A quantity of 0.5 ml was removed for solubilization and counting. All other samples received 0.5 ml of distilled H$_2$O. A quantity of 3 ml of TS-2 tissue solubilizer (RPI International) was added to all samples followed by incubation for 48 hours at 50° C. The solution was then neutralized with 120 μl of acetic acid, 17.5 ml of Liquiflor ® counting cocktail (NEN/DuPont) was added, and the samples were counted. The tissue content of 1-O-octadecyl-sn-glycero-P-AZT and metabolites was determined based on the specific activity. The results are expressed as nmol AZT/gm tissue or per ml of plasma. Drug retention over time measured was determined by integrating the area under the curve (AUC) for each tissue. Results are as follows and are illustrated graphically in FIGS. 1 to 14:

a. Plasma levels

Plasma samples were extracted by the method of Folch, J., et al. (JBC, 1957) and the lipids chromatographed on thin layers of silica which were scanned with a radioscanner. Spots corresponding to 1-O-octadecyl-sn-glycero-3-P-AZT-$^3$H and the $^3$H-AZT reference standards were identified and the radioactivity measured. Orally administered 1-O-octadecyl-sn-glycero-3-P-AZT-$^3$H gave initial plasma levels of 7 nmol/ml at 1 hr as shown in FIG. 1 and Table 1. Plasma levels >1 nmol/ml were observed throughout the 24 hr. period and seemed to rise slightly between 12 and 24 hours to a final level of 3.0 nmol/ml (3 μM). The IC$_{50}$ of 1-O-octadecyl-sn-glycero-3-P-AZT ranged from 0.4 to 1.1 μM in LAV-infected HT4-6C cells as measured by the method of Larder et al., Science 243; 1731-34 (1989).

Drug availability was also determined by calculating the integrated dose during the measurement period (area under the curve, or AUC). AUC was determined and compared to that of free AZT. The AUC ratio of 1-O-octadecyl-sn-glycero-3-P-AZT/AZT was 1.38, indicating excellent gastrointestinal absorption of the liponucleotide.

b. Stomach, duodenum and jejunum

Figure 2:
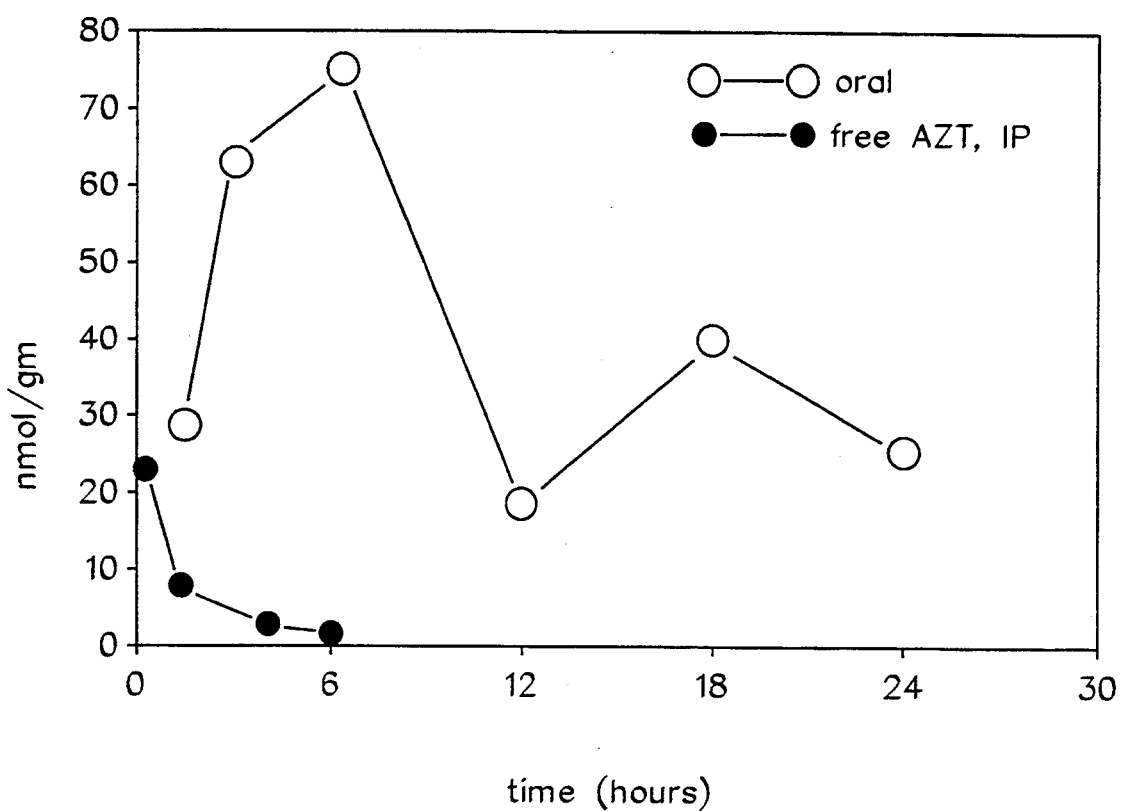
Figure 3:
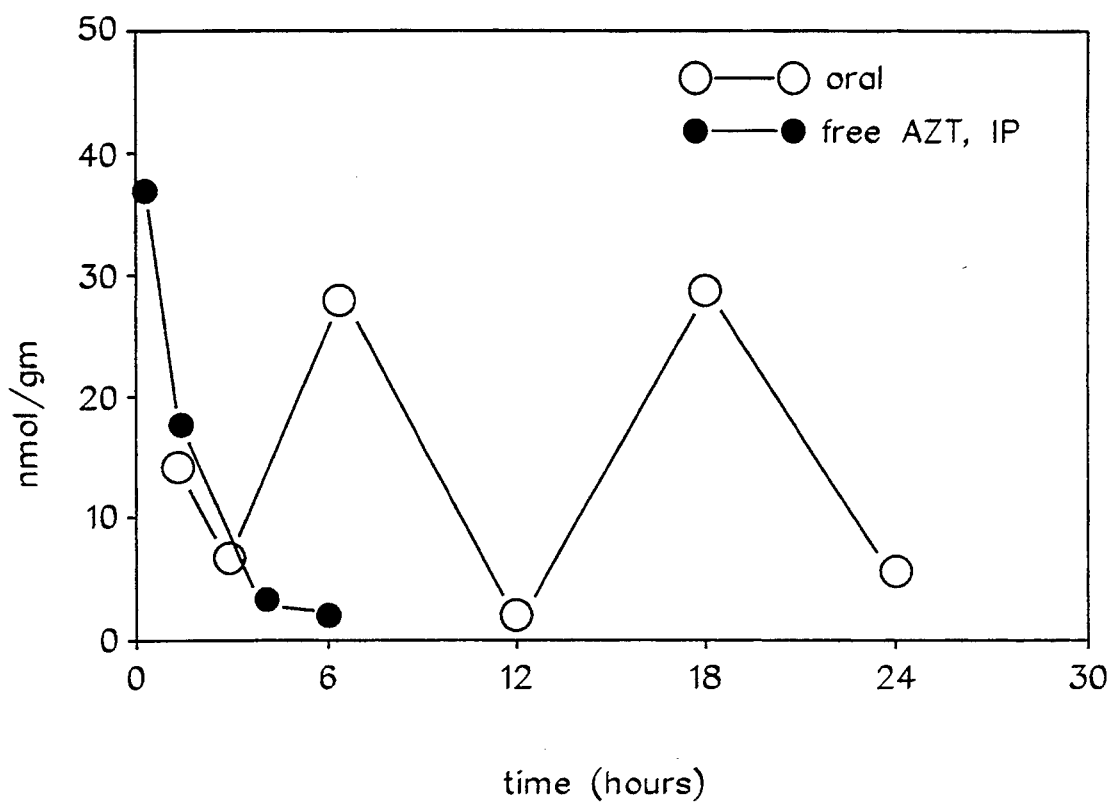
Figure 4:
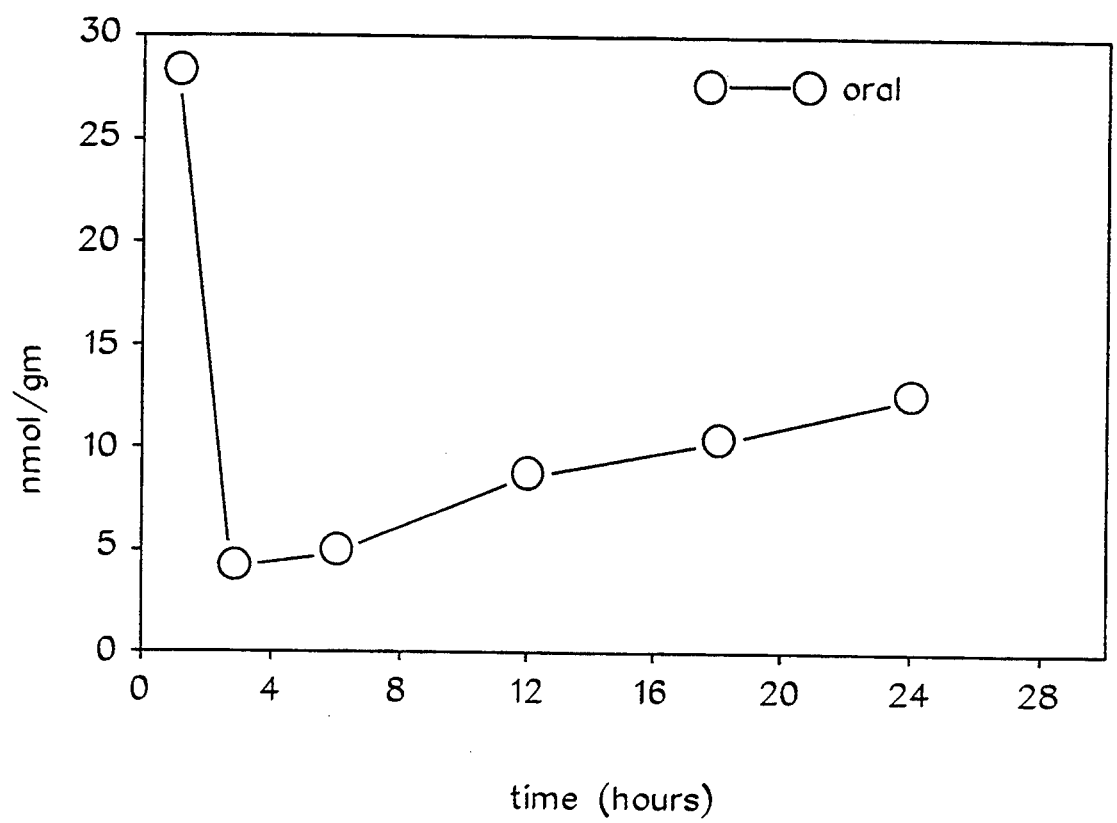
Figure 5:
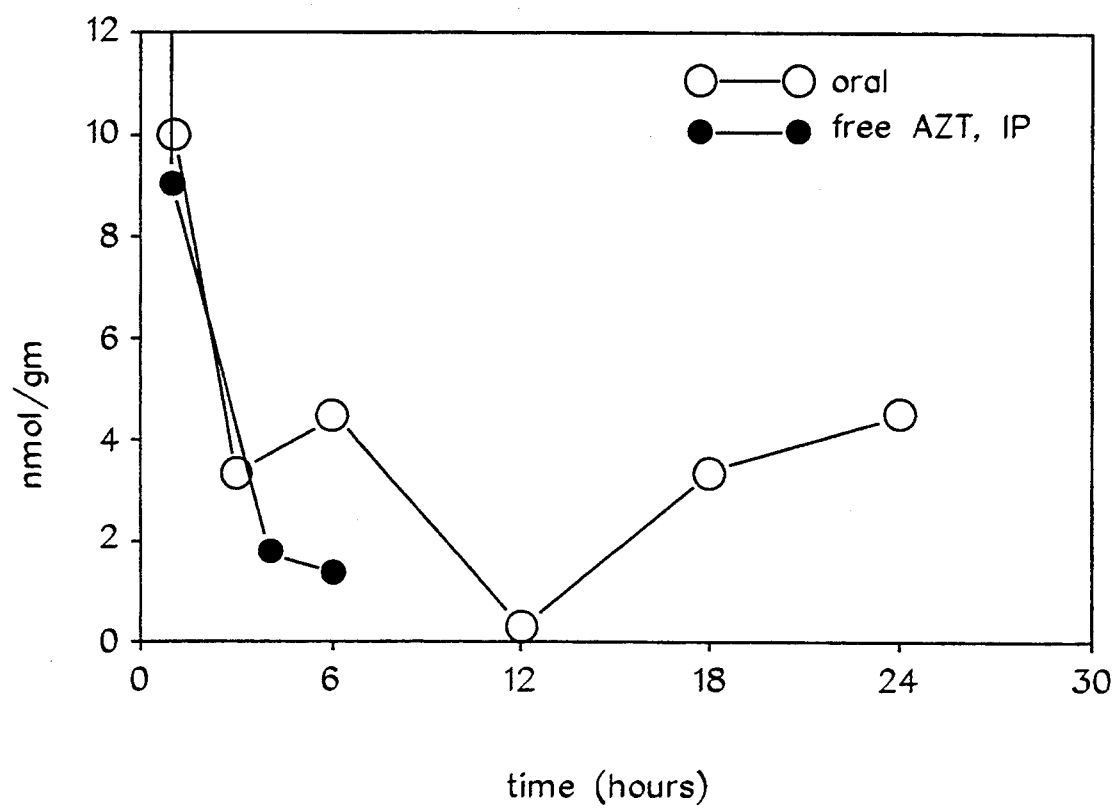
Figure 6:
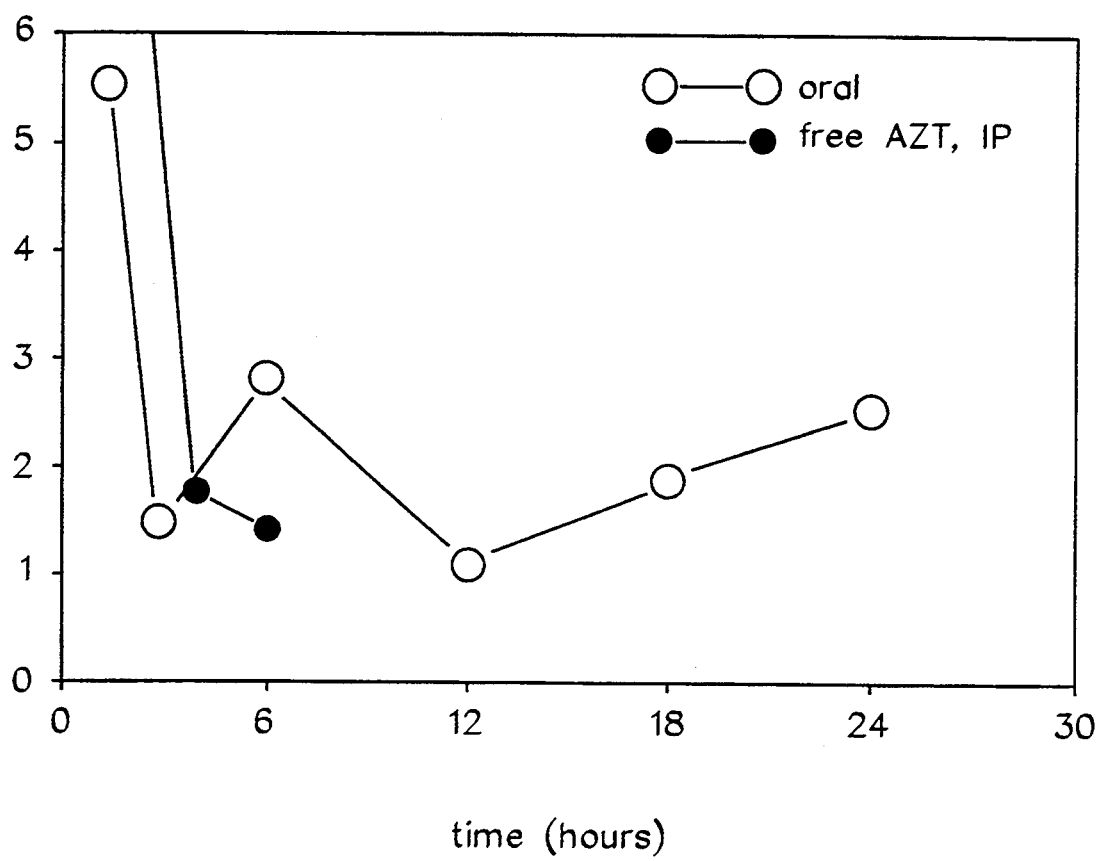
Figure 7:
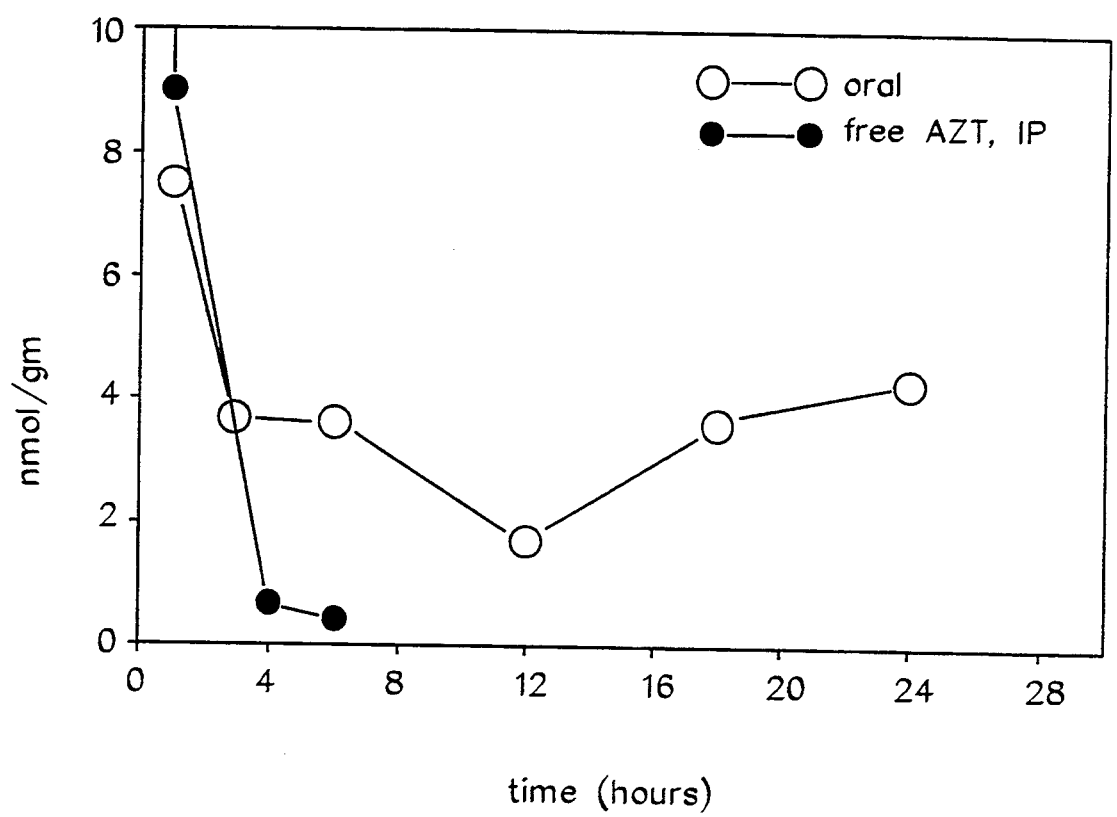
Figure 8:
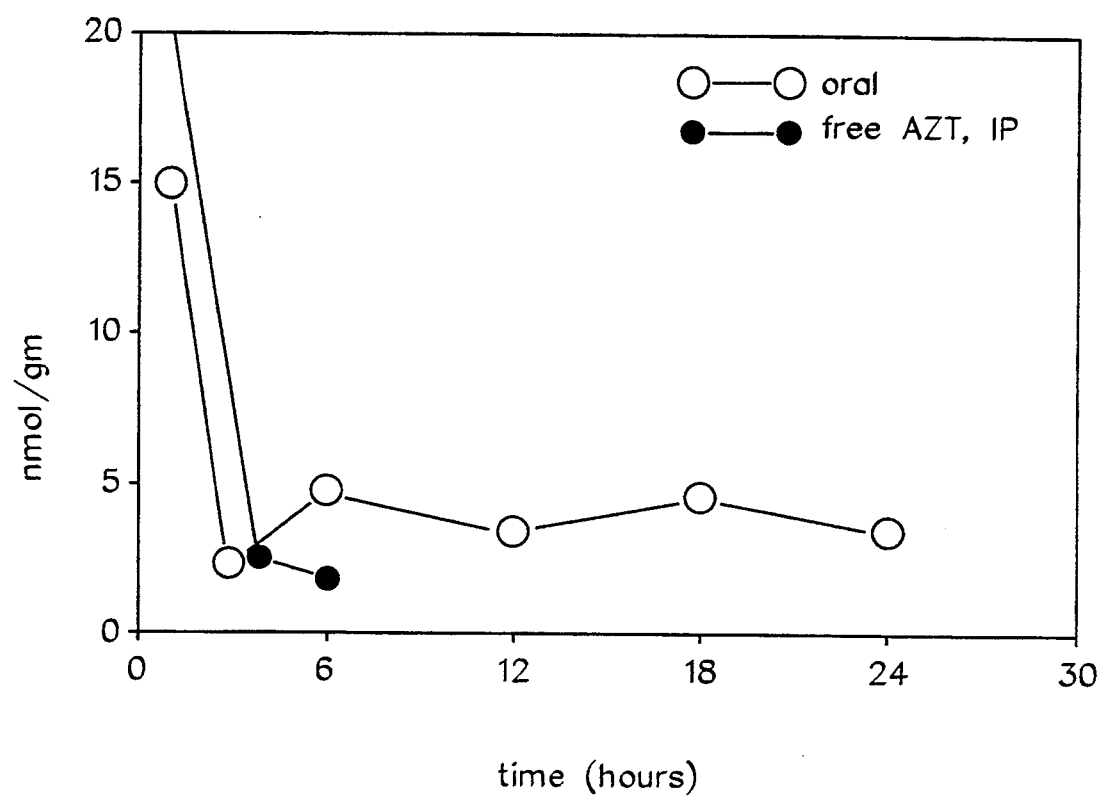
FIGS. 8, 9, 10, and 11 are graphs showing the comparative levels of AZT in the kidney, skin, skeletal, and heart muscle tissues respectively.

Levels of batyl-P-AZT (bPAZT) in stomach peaked at 75 nmol/ml at 6 hr. and declined to 26 nmol/gm at 24 hr. (FIG. 2). Drug levels in the duodenum also peaked at 28 nmol/gm at 6 hr. and were variable thereafter (FIG. 3). bPAZT levels in jejunum were highest at 1 hr., declined to 5 nmol/gm, rising gradually thereafter to 12 nmol/gm at 24 hr. (FIG. 4).

c. Liver, spleen and lymph nodes

Figure 9:
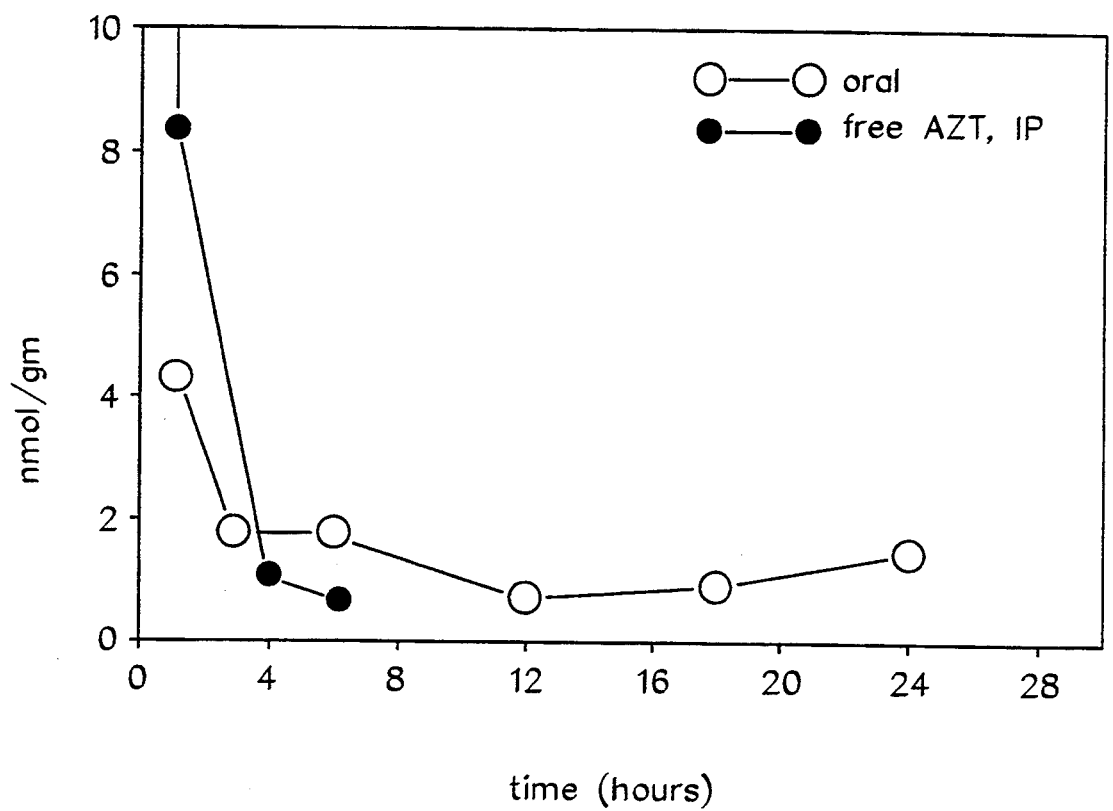
Figure 10:
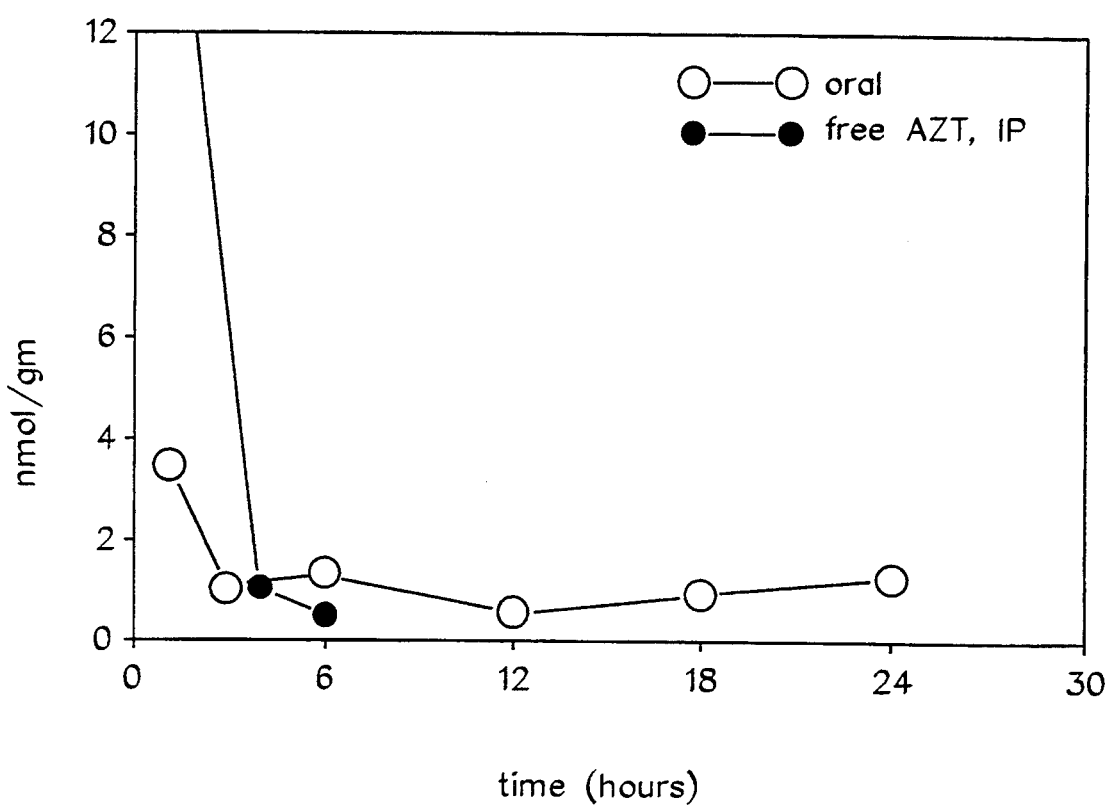
Figure 11:
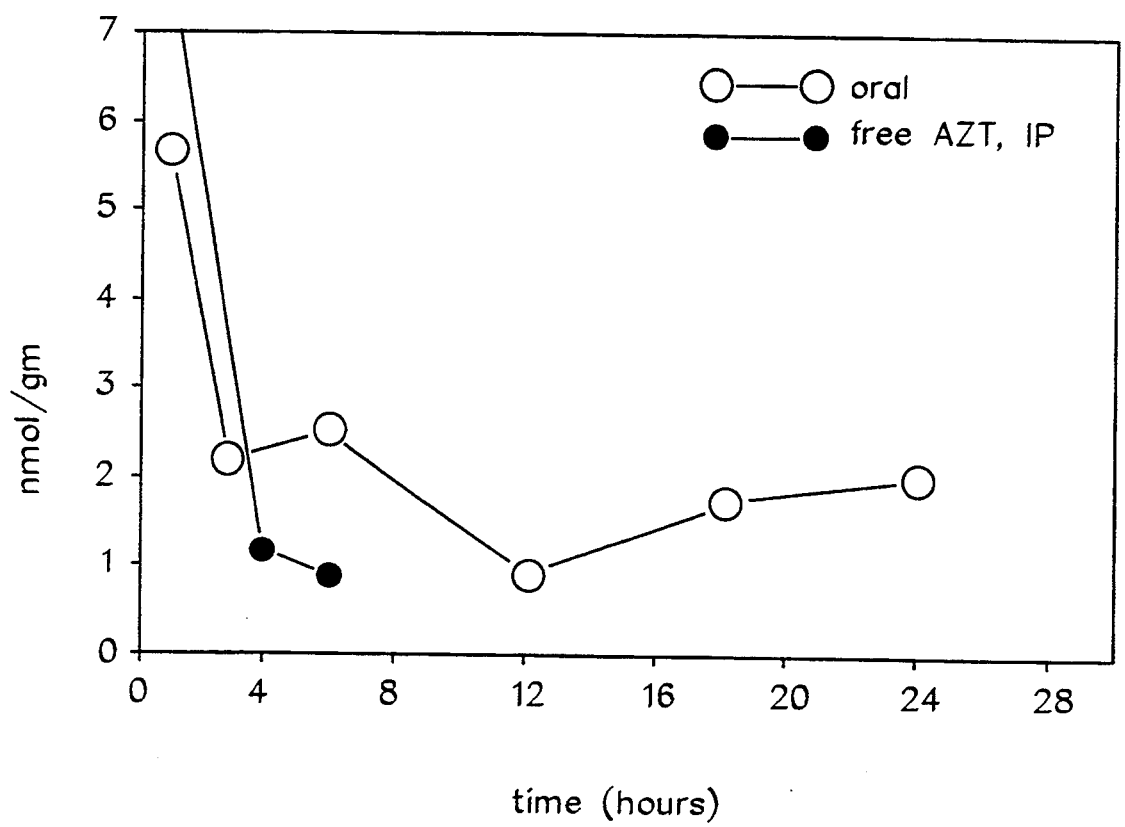
Figure 12:
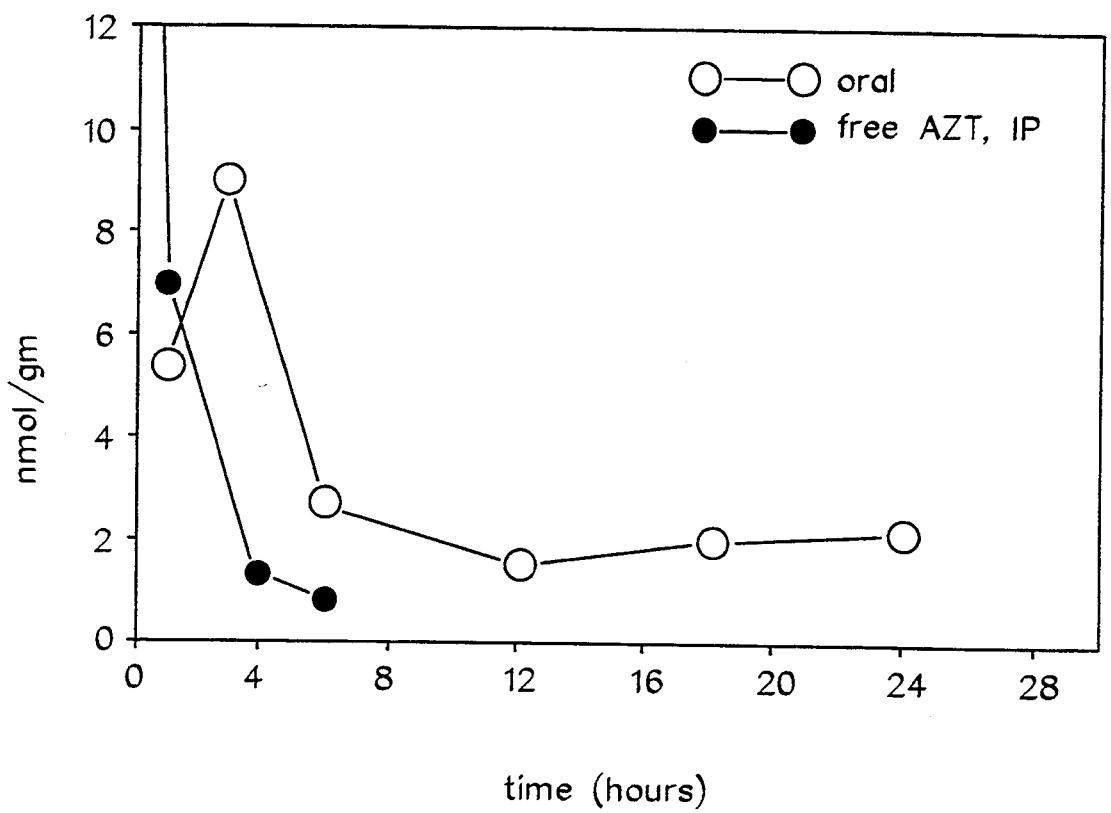
FIGS. 12 and 13 are graphs showing the comparative levels of AZT in the lung and adrenals respectively.
Figure 13:
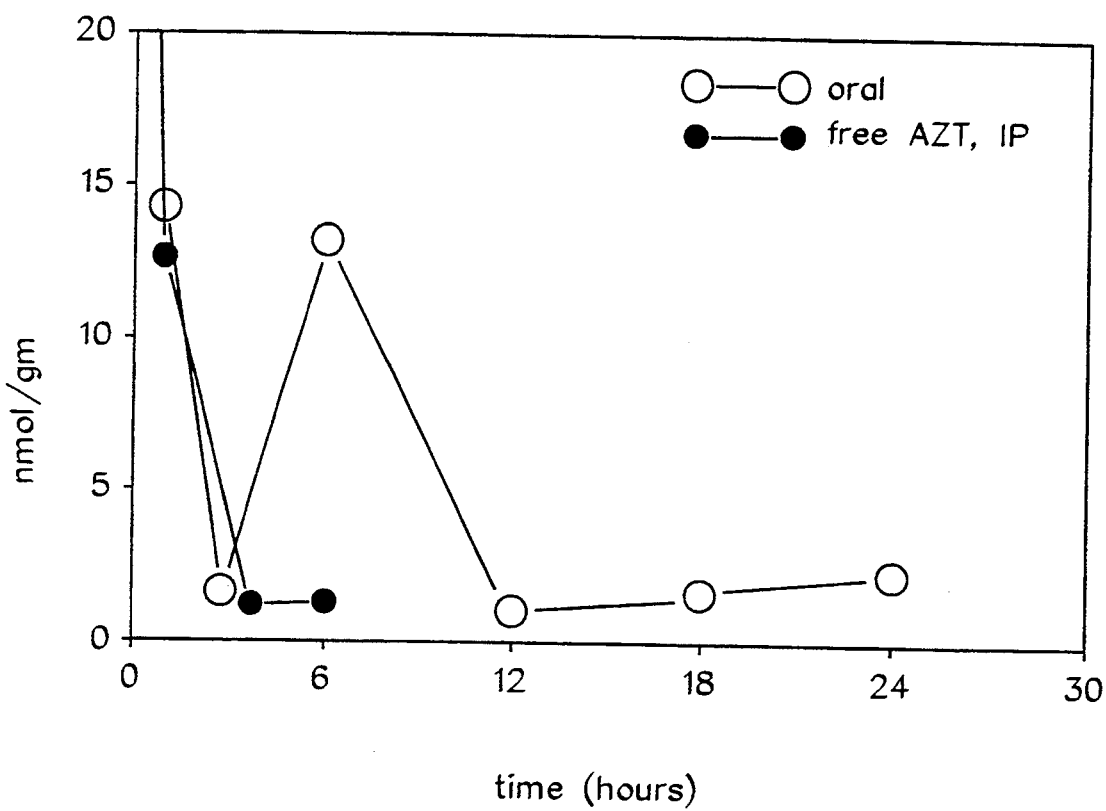

In these tissues, bPAZT levels were maximal at 1 hr., ranging from 5.5 to 10 nmol/gm. Tissue levels declined gradually thereafter to 2.5 (spleen, FIG. 5), and 4.3 nmol/gm (liver, FIG. 6 and lymph nodes, FIG. 7) at 24 hr.

d. Kidney, skin, skeletal and heart muscle bPAZT levels in kidney (FIG. 8) were highest at 1 hr. (15 nmol/gm) declining to 3.6 nmol/gm at 24 hrs (FIG. 9). Similar bPAZT profiles were also seen in skeletal muscle (FIG. 10) and heart (FIG. 11).

d. Lung and adrenal bPAZT levels in lung were highest at 1 and 3 hrs. at 1.4 nmol/gm as shown in FIG. 12. From 6 to 24 hr. drug levels ranged from 1.4 to 2.4 nmol/gm. Adrenal levels were variable (FIG. 13 ).

c. Brain

Figure 14:
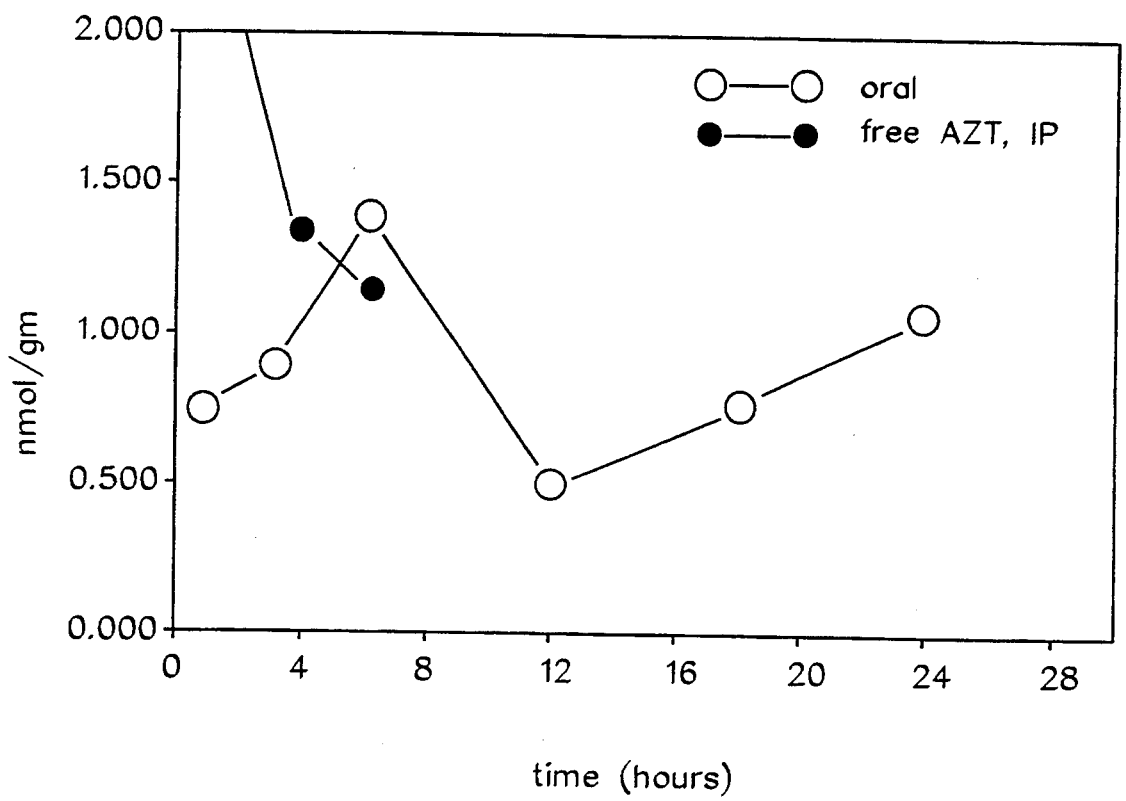
FIG. 14 is a graph showing the comparative levels of AZT in brain.

Brain levels of bPAZT-$^3$H were maximal at 6 hours at 1.4 nmol/gm as shown in FIG. 14. Plasma levels at 6 hrs. were 3.14 nmol/ml, making it unlikely that the material measured in brain plasma background. At 24 hours brain bPAZT levels continued to be significant at 1.1 nmol/gm (versus 3.0 nmol/ml in plasma).

d. Urine and fetes At 6 hrs., 40±16% of the total administered dose of bPAZT-$^3$H was recovered in the urine and 0.41±0.11 percent of the administered dose was recovered in the feces.

TABLE 2

Pharmacokinetics of lipid derivatives of AZT in vivo
Free AZT in plasma:nmol/ml

| Time | Batyl AZT | Free AZT |
|---|---|---|
| 15 min | ND | 49.3 |
| 1 hour | 7.03 | 12.4 |
| 3 hour | 1.73 | ND |
| 4 hour | ND | 1.5 |
| 6 hour | 3.16 | 1.1 |
| 12 hour | 1.18 | ND |
| 18 hour | 2.16 | ND |
| 24 hour | 3.02 | ND |

Conclusions: Oral 1-O-octadecyl-sn-glycero-3-phospho AZT-$^3$H Plasma and tissue levels of AZT were much higher following the oral administration of 1-O-octadecyl-sn-glycero-3-phosphoAZT(bPAZT) than those observed above with free AZT. With bPAZT tissue levels of 1.5 to 5 nmol/gm were detected at 24 hrs. This compares very favorably to tissue levels obtained with intraperitoneal administration of free AZT.

EXAMPLE 18

Single-Dose 1-O-octadecyl-sn-glycero-3-phospho-AZT Oral Administration Compared to Continuous Oral AZT Administration Treatment of Rauscher Leukemia Virus-Infected Mice:

Female BALB/C mice were infected with 1×10$^4$ plaque-forming units (PFU) of Rauscher leukemia virus complex (RLV) on day 0. Control animals were injected with saline. Beginning on day 2, groups of the infected mice as indicated in FIG. 15 were treated with AZT at doses from about 1.0 mg/kg/day to 15.0 mg/kg/day for 21 days either by offering AZT in drinking water or by gavaging with batyl-PAZT once a day. On day 23 post-inoculation, the mice in both treatment protocols were sacrificed, and the spleen weights of the animals were determined. The mean spleen weights, indicating relative level of virus infection, for each dose level in the two protocols, are represented in the bar graphs of FIG. 15. The effective doses (ED50) of daily batyl-P-AZT given by a single oral administration and AZT given by oral administration in the drinking water were comparable.

It is apparent from the foregoing that other 1-O-alkyl glycerol phosphate derivatives of therapeutic drugs can be substituted in the Examples 2-11 to obtain similar results of delivering a drug, otherwise orally non-bioavailable, more effectively through the oral route. It should be further emphasized that the present invention is not limited to the use of any particular drug or therapeutic agent in the compounds of the invention; rather the beneficial results of the invention flow from the synthesis of 1-O-acyl-, 1-O-alkyl-, 1-S-acyl-, or 1-S-alkyl-sn-glycerophosphate prodrugs of these drugs and agents. Thus, regardless of whether a specific drug or agent is presently known, or whether it becomes known in the future, the methods of forming the presently contemplated lipid prodrugs therefrom are based on established chemical techniques, as will be apparent to those of skill in the art, and therefore these compounds are broadly enabled by the preceding disclosure. It should be emphasized again that the present syntheses are broadly applicable to formation of compounds from essentially all drugs having an appropriate structure, and the effectiveness of which can be improved by preparing a lipid prodrug form for use in the practice of the invention.

Accordingly, the invention may be embodied in other specific forms without departing from its spirit or essential characteristics. The described embodiments are to be considered in all respects only as illustrative and not restrictive, and the scope of the invention is, therefore, indicated by the appended claims rather than by the foregoing description. All modifications which come within the meaning and range of the lawful equivalency of the claims are to be embraced within their scope.

What is claimed is:

1. A method of converting a drug that is unavailable or poorly available in a mammal through the oral route of administration to an orally available form, comprising:
   (a) covalently linking a lipid species selected from the group consisting of 1-O-alkyl-sn-glycerol-3-phosphates, and 1-O-acyl-sn-glycerol-3-phosphates to a functional group of said drug either directly through the phosphate group of the lipid species or through a multifunctional linker molecule to form a lipid derivative of the drug;
   (b) recovering the lipid derivative of the drug from the linking reaction mixture of step (a); and
   (c) incorporating the lipid derivative of the drug into a therapeutic formulation suitable for oral administration.

2. The method of claim 1 wherein said lipid derivative is a 1-O-alkyl-sn-glycerol-3-phosphate derivative of a drug, of the formula

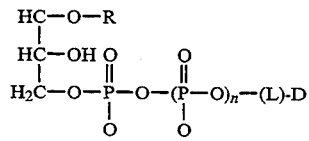 [I]

wherein R is a substituted or unsubstituted, saturated or unsaturated, straight or branched chain, or cyclic $C_{1-24}$ alkyl group, covalently linked to the glycerol moiety in an ether linkage;

n=0 to 2;

L is a linking molecule, of the formula X—(CH$_2$)$_n$—Y wherein X and Y are functional groups independently selected from hydroxyl, sulfhydryl, carboxyl and amine groups, and n=1 to 24; or L is absent; and D is a drug having a functional group selected from the group consisting of hydroxyl, sulfhydryl, carboxyl, or amino groups.

3. The method of claim 2, wherein the drup is an anticancer nucleoside having a carboxyl, hydroxyl, or amino group available for covalent binding.

4. The method of claim 3, wherein the drug is 9-β-D-arabinofuranosylcytosine (ara-C), 5-fluorouridine, 6-mercaptopurine riboside, 9-β-D-arabinofuranosyladenine (ara-A), or 2'-arafluoro-2-chloro-deoxyadenosine.

5. The method of claim 2, wherein the drug is 5-amino-4-imidazole carboxamide ribonucleoside (AICA-riboside).

6. The method of claim 2, wherein D is a therapeutic peptide, or a peptidomimetic of from 3 to 35 amino acid residues or analogues thereof.

7. The method of claim 6, wherein the drug is n-muramyl tripeptide.

8. The method of claim 6, wherein the drug is enalkiren.

9. The method of claim 2, wherein the drug is selected from the group consisting of antibiotics of the penicillin and cephalosporin class.

10. The method of claim 9, wherein the drug is selected from the group consisting of penicillin G, cefazolin, ceftazidime, ceftriaxone, piperacillin.

11. The method of claim 1, wherein said drug is 3'-azido-3'-deoxythymidine (AZT).

12. The method of claim 1, wherein said drug is 3'-azido-3'-acycloguanosine (ACG).

* * * * *

UNITED STATES PATENT AND TRADEMARK OFFICE
CERTIFICATE OF CORRECTION

PATENT NO. : 5,411,947

DATED : May 2, 1995

INVENTOR(S) : Hostetler et al.

It is certified that error appears in the above-indentified patent and that said Letters Patent is hereby corrected as shown below:

Column 4, lines 50-57, and column 22, lines 34-41, make changes to formula (I), so that it appears as shown on the attached page.

Signed and Sealed this

Fifth Day of March, 1996

Attest:

BRUCE LEHMAN

Attesting Officer    Commissioner of Patents and Trademarks

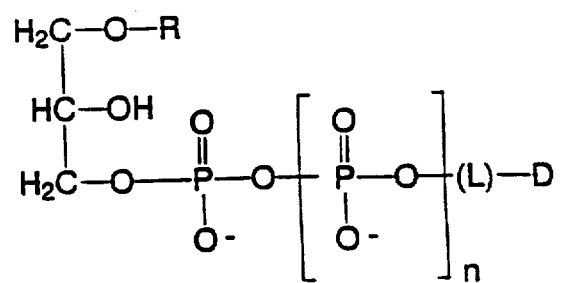

UNITED STATES PATENT AND TRADEMARK OFFICE
CERTIFICATE OF CORRECTION

PATENT NO. : 5,411,947
DATED : May 2, 1995
INVENTOR(S) : Hostetler, et. al.

It is certified that error appears in the above-identified patent and that said Letters Patent is hereby corrected as shown below:

Column 24, lines 6-7, please replace "3'-azido-3'-acycloguanosine (ACG)" with -- acycloguanosine --.

Signed and Sealed this

Twenty-third Day of December, 1997

Attest:

BRUCE LEHMAN

Attesting Officer

Commissioner of Patents and Trademarks